United States Patent [19]

Williams

[11] Patent Number: 5,310,539
[45] Date of Patent: May 10, 1994

[54] MELANIN-BASED AGENTS FOR IMAGE ENHANCEMENT

[75] Inventor: Robert F. Williams, San Antonio, Tex.

[73] Assignee: Board of Regents, The University of Texas System, Austin, Tex.

[21] Appl. No.: 685,937

[22] Filed: Apr. 15, 1991

[51] Int. Cl.$^5$ .................... A61K 49/00; A61K 49/02
[52] U.S. Cl. ........................................ 424/9; 523/375
[58] Field of Search ................ 420/1; 424/1.1, 490, 424/491, 9; 252/301.18, 645; 534/10; 523/375

[56] References Cited

U.S. PATENT DOCUMENTS

| | | | |
|---|---|---|---|
| 4,247,406 | 1/1981 | Widder et al. | 252/62.53 |
| 4,352,751 | 10/1982 | Wieder | 260/112 |
| 4,370,476 | 1/1983 | Usher | 536/113 |
| 4,421,671 | 12/1983 | Cusano | 252/301.4 |
| 4,423,158 | 12/1983 | Porath | 521/32 |
| 4,432,907 | 2/1984 | Wieder | 260/420.2 |
| 4,452,773 | 6/1984 | Molday | 424/1.1 |
| 4,472,509 | 9/1984 | Gansow | 436/548 |
| 4,639,365 | 1/1987 | Sherry | 424/9 |
| 4,647,447 | 3/1987 | Gries et al. | 424/9 |
| 4,698,374 | 10/1987 | Gallas | 523/106 |
| 4,731,239 | 3/1988 | Gordon | 424/9 |
| 4,735,210 | 4/1988 | Goldenberg | 128/654 |
| 4,735,796 | 4/1988 | Gordon | 424/9 |

(List continued on next page.)

FOREIGN PATENT DOCUMENTS

| | | |
|---|---|---|
| WO85/05554 | 12/1985 | European Pat. Off. . |
| 0184899AI | 6/1986 | European Pat. Off. . |
| 0186947AI | 7/1986 | European Pat. Off. . |
| PCT/US92/-03177 | 4/1992 | PCT Int'l Appl. . |
| 1529150 | 9/1977 | United Kingdom . |
| 2137612A | 10/1984 | United Kingdom . |

OTHER PUBLICATIONS

Monograph No. 5629, Merck Index, p. 5632, 10th Edition, 1983.
Aime et al. "NMR Studies of L-Dopa Melanin-Manganese (II) Complex in Water," Journal of Inorganic Biochemistry, 36(1), 1989, pp. 1-9.
Lauffer et al., "Preparation and Water Relaxation Properties of Proteins Labeled with Paramagnetic Metal Chelates," Magnetic Resonance Imaging, vol. 3, No. 1, 1985, pp. 11-16.
Ishiwata et al., "Feasibility Study of Fluorine-18 Labeled Dopa for Melanoma Imaging," Abstract No. 111705p, Nucl. Med. Biol., 16(4):371-4, (1989). File Server STN, Karlsruhe DE, File Chemical Abstracts, vol. 111, No. 13, published in Columbus, Ohio, USA.
Dawson et al., "Progress Toward the Synthesis of Polymerically Bound Chelating Agents for Iron(III) and the Development of a New Assay Method for Determining (List continued on next page.)

Primary Examiner—Robert L. Stoll
Assistant Examiner—Lara E. Chapman
Attorney, Agent, or Firm—Arnold, White & Durkee

[57] ABSTRACT

The present invention involves an image-enhancing agent comprising melanin combined with an essentially non-dissociable signal-inducing metal. The signal-inducing metal has an association constant for its melanin combination of at least about $10^{20}$. Upon suspension or dissolution in water the metal remains undissociated. A preferred signal-inducing metal is paramagnetic or superparamagnetic, of course for magnetic resonance imaging. A preferred paramagnetic or superparamagnetic metals are gadolinium, iron, nickel, copper, erbium, europium, praseodymium, dysprosium, holmium, chromium or manganese. Gadolinium is the most effective metal. The metal is incorporated into the melanin in an ionic or particulate form. Metals may be utilized which are particularly useful to modify ultrasound images by the enhancement of the image obtained from emission and detection of high-frequency soundwaves. Metals emitting gamma particles may also be utilized to enhance images resulting from gamma particle emission scanning. $^{51}$Chromium, $^{68}$gallium, $^{99m}$technitium and $^{111}$indium are preferred metals for gamma particle scanning. Additionally, native or synthesized melanin, in and of itself is an effective MRI image-enhancing agent.

14 Claims, 18 Drawing Sheets

U.S. PATENT DOCUMENTS

| | | | |
|---|---|---|---|
| 4,770,183 | 9/1988 | Groman et al. | 128/654 |
| 4,822,594 | 4/1989 | Gibby | 424/9 |
| 4,904,479 | 2/1990 | Illum | 424/490 |
| 4,957,939 | 9/1990 | Gries et al. | 514/492 |
| 4,963,344 | 10/1990 | Gries et al. | 424/9 |
| 4,968,980 | 1/1991 | Jacobsen | 424/9 |
| 4,985,233 | 1/1991 | Klaveness et al. | 424/9 |
| 5,021,236 | 6/1991 | Gries et al. | 424/9 |
| 5,057,302 | 10/1991 | Johnson et al. | 424/1.1 |
| 5,137,711 | 8/1992 | Weber et al. | 424/9 |
| 5,185,368 | 2/1993 | Peter et al. | 514/476 |
| 5,187,207 | 2/1993 | Gallas et al. | 523/106 |

OTHER PUBLICATIONS

Iron Chelator Effectiveness," *Development of Iron Chelators for Clinical Use*, pp. 201–209 (1981).

Dialog Search Report, 97 pages (23 Jun. 1990).

Brasch et al., "Contrast-Enhanced NMR Imaging: Animal Studies Using Gadolinium-DTPA Complex," *A.J.R.*, 142:625–30 (1984).

Buonocore, et al., "Potential Organ Specific MRI Constrast Agents for Liver and Spleen: Gadolinium Labelled Liposomes," *Proc. Soc. Mag. Resonance in Med.*, 838–839 (1985).

Burnett et al., "Gadolinium Oxide: A Prototype Agent for Contrast Enhanced Imaging of the Liver and Spleen with Magnetic Resonance," *Magnetic Resonance Imaging*, 3:65–71 (1985).

Chen et al., "Paramagnetic Metalloprophyrins as Potential Contrast Agents in NMR Imaging,," *Fed. Euro. Biochem. Soc.*, 168(1):70 (1984).

Desreux, "Nuclear Magnetic Resonance Spectroscopy of Lanthanide Complexes with a Tetraacetic Tetraaza Macrocycle. Unusual Conformation Properties," *Inorganic Chemistry*, 19:1319–24 (1980).

Enochs et al., "Sources of the Increased Longitudinal Relaxation Rates Observed in Melanotic Melanoma. An in vitro Study of Synthetic Melamins.," *Invest. Radiol.*, 24(10):794–804, (Oct. 1989).

Geraldes et al., "Magnetic Field Dependence of Solvent Proton Relaxation Rates Induced by $Gd^{3+}$ Complexes of Various Polyaza Macrocyclic Ligands: Implications for NMR Imaging," *Magnetic Resonance in Medicine*, 3:242–50 (1986).

Goldstein et al., "Gadolinium DTPA (An NMR Proton Imaging Contrast Agent): Chemical Structure, Paramagnetic Properties and Pharmacokinetics," *Physiol. Chem. & Phys. & Med. NMR*, 16:97–104 (1984).

Hintz et al., "Metal Ion-induced Activation of Molecular Oxygen in Pigmented Polymers," *Biochim. Biophys. Acta*, 883:41–45 (Aug. 6, 1986).

Lettvin et al., "Gd(TTHA): An aqueous Carbon-13 Relaxation Reagent," *J. Mag. Res.*, 28:459–61 (1977).

Martell, A., "The Design and Synthesis of Chelating Agents," *Development of Iron Chelators for Clinical Use*, pp. 67–104 91981).

Mirowitz et al., *AJK Am. J. Roentgenol*, 154, 369–73 (Feb. 1990).

Runge, et al., "Work in Progress: Potential Oral and Intravenous Paramagnetic NMR Contrast Agents," *Radiol.*, 147:789–91, (Jun. 1983).

Sarna et al., "Ion Exchange in Melanin: An Electron Spin Resonance Study with Lanthanide Probes," *Science*, 192:1132–4, (Jun. 11, 1976).

Weinmann et al., "Characteristics of Gadolinium-DTPA Complex: A Potential NMR Contrast Agent," *A.J.R.*, 142:619–24 (1984).

Wolf, "Contrast Enhancement in Biomedical NMR," *Physiol. Chem. & Phys. & Med. NMR*, 16:93–95 (1984).

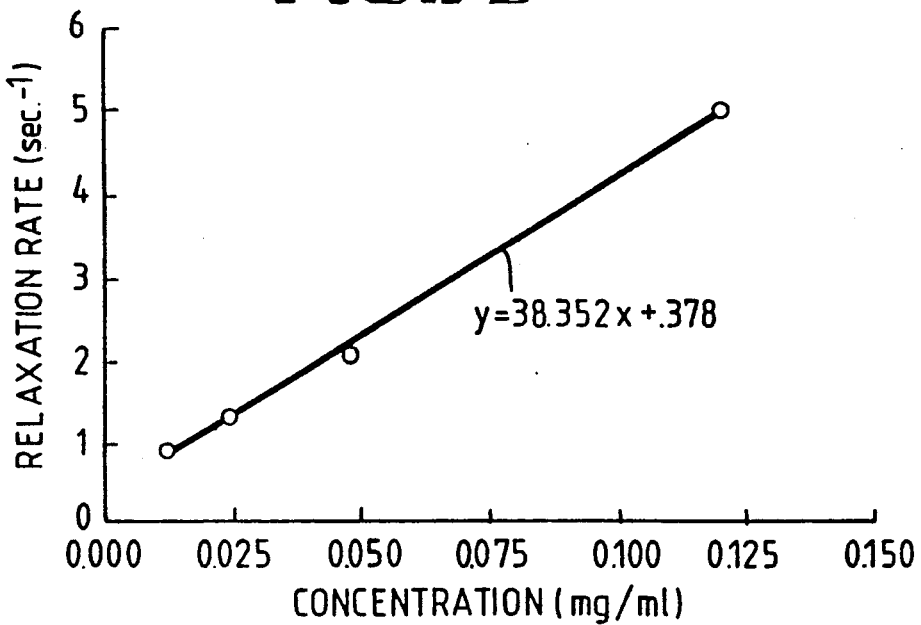
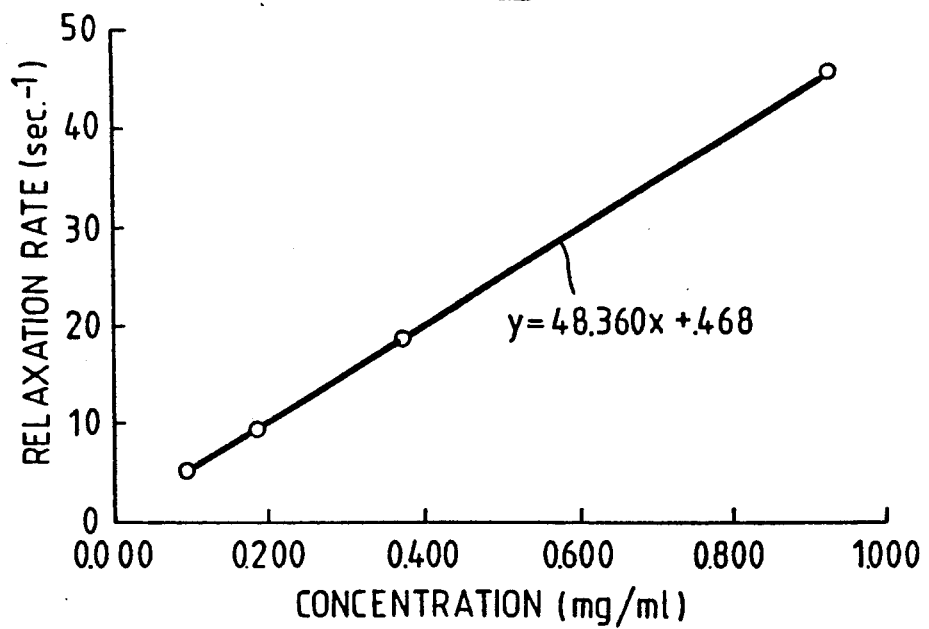

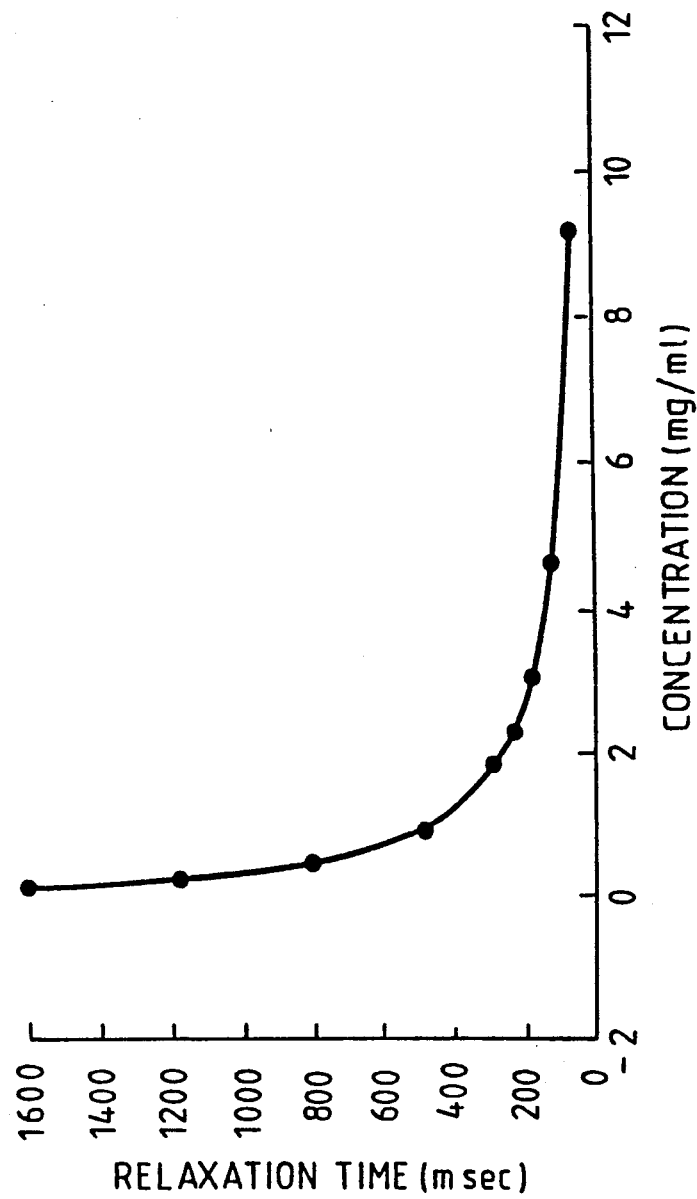

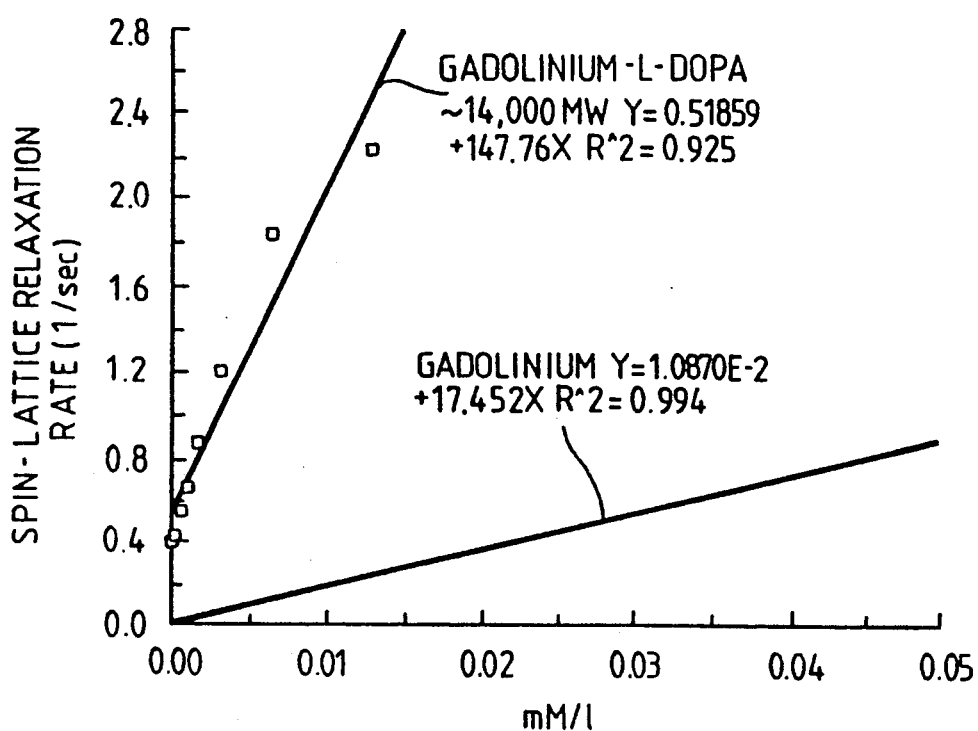
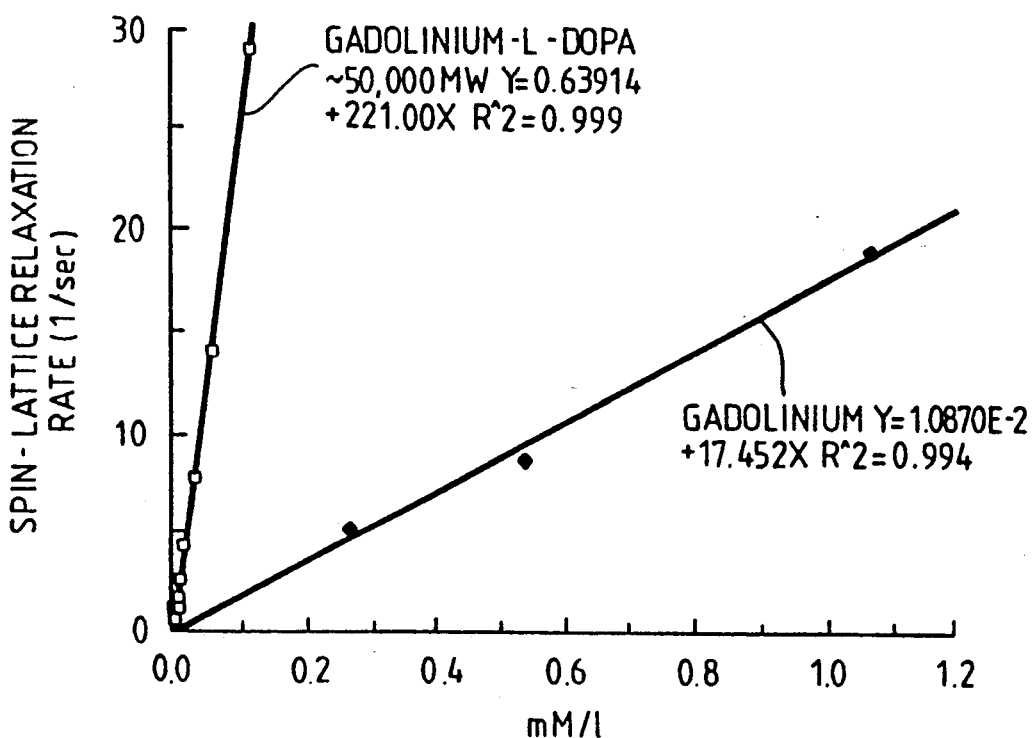

MELANIN-BASED AGENTS FOR IMAGE ENHANCEMENT

BACKGROUND OF THE INVENTION

The present invention relates to image-enhancing agents, contrast agents or spectral shift agents to enhance tissue or organ images or nuclear spectra obtained from live animals with magnetic resonance imaging (MRI) or spectroscopy (MRS), radioisotope scanning or ultrasound imaging.

Magnetic resonance imaging is a medical procedure that takes advantage of the magnetic spin properties of nuclei to create an image fundamentally like that of the more widely known X-ray procedure the CT scan. The nucleus of an atom contains neutrons and protons. Atoms which have an odd number of neutrons or protons have a non-zero spin quantum number (I). These atoms can be thought to behave like small spinning spheres. Because the nuclei have positive charges, the spinning produces a magnetic moment ($\overline{U}$), analogous to an electric current in a closed loop of wire. When exposed to a magnetic field these dipoles align themselves with the magnetic field. The spin (magnetic moment) vectors experience a torque when subjected to a magnetic field. Due to this torque, the nuclei process about the axis of the magnetic field at a rate given by the Larmor relationship:

$$f = w/2\pi = \gamma Bo/2\pi$$

f = resonance frequency in Hertz (Hz)
w = the angular frequency in radians per second
$\gamma$ = magnetic gyric ratio
Bo = static magnetic field
$\gamma$ = a nuclear constant characteristic of the isotope The resonance frequency of a nucleus is a function of its magnetogyric ratio (a constant for the particular nucleus being studied) and the strength of an applied magnetic field (Larmor equation). The magnetogyric ratio of a nucleus relates the magnetic moment and the nuclear spin quantum number (I). The spin quantum number depicts the number of energy states that a nucleus can have; a nucleus has 2I+1 energy levels. The hydrogen nucleus (a proton) has a nuclear spin of $\frac{1}{2}$, and thus two possible spin states. In nuclear magnetic resonance spectroscopy (NMR), the magnetic moment is shown as revolving around a fixed magnetic field (FIG. 1) at a fixed frequency. In a sample, large numbers of nuclei are revolving around this field in one of the two possible spin states, creating a "macroscopic magnetization" M parallel to the magnetic field. There are more nuclei in the low-energy spin state when there is no outside influence (FIG. 2).

Resonance is the induction of a transition between two different energy states. The nuclei that lends itself best to magnetic resonance imaging is the proton, the major isotope of hydrogen. Hydrogen has a very large abundance in biological systems in water ($E10^{23}/cm^3$) as well as in other biochemical molecules and has the required magnetic moment. The energy necessary to produce a transition between the two spin states of hydrogen ($+\frac{1}{2}$ and $-\frac{1}{2}$) is the difference in energy ($\Delta E$) between these spin states. In MRI, resonance occurs when radiofrequency (RF) energy is applied at the Larmor frequency, flipping the magnetic moments from their $m = +\frac{1}{2}$ (lower energy) to their $m = -\frac{1}{2}$ (higher energy) states. Magnetic resonance absorption can only be detected by transverse magnetization (magnetization perpendicular to Bo). Only the transverse component, Mxy, is time dependent and therefore according to Faraday's law of induction, only time dependent magnetization can induce a voltage in a receiver coil. Transverse magnetization is generated when a radiofrequency (RF) field of amplitude B., rotating synchronously with the processing spins is applied.

When the RF field acts in a direction perpendicular to the main field, the effect is to rotate the magnetization away from the rest state. The macroscopic magnetization experiences a torque of the RF field, forcing the magnetization to rotate about it. If the duration of the B. field is such that the net magnetization is rotated by an angle of 90°, it will become transverse or perpendicular to the stated field (FIG. 3). The angle of rotation $\theta$, the RF flip angle, is given by the Ernst equation.

$$\theta = \gamma B_1 \tau$$

$B_1$ = amplitude of the FR field
$\pi$ = duration

Once the RF field is removed, the magnetization is subjected to the effect of the static magnetic field and processes about it. With a detection coil positioned with its axis along the y axis, the AC voltage induced in the coil is given by $$\gamma \delta M xy^\circ \cos w\tau$$

Mxy° = initial transverse magnetization following a 90 degree RF pulse
$\tau$ = time interval between the rotation The transverse magnetization decays to zero exponentially with a time constant T2*.
Therefore:

$$\gamma \delta M xy^\circ e^{-\tau/T2*} \cos w\tau$$

This equation represents a damped oscillation that is called the induction decay or FI0 signal. As the transverse magnetization decays to zero with time, the longitudinal magnetization increases back to its equilibrium value. This return to equilibrium values is termed relaxation. RF stimulation causes the nuclei to absorb energy transferring them to the excited state. The nuclei can return to the ground state by transferring energy to their surroundings, the so called lattice. This method of relaxation is called spin-lattice relaxation (T1). (see FIG. 4) Components of M, after being rotated to the x'y' plane, (FIG. 5) return to their original magnetization values in a time (T2), the "spin-spin" relaxation time. In the T2 relaxation process, nuclei in the excited and ground state exchange energy with each other. Thus T2 measures the amount of time necessary for the nuclei to get out of phase with each other and return to the original random state. Both T1 and T2 relaxation times of a nuclei can vary widely from milliseconds to minutes depending upon the nuclei and the environment surrounding them. The primary task of magnetic resonance imaging is soft tissue contrast and the detection of low-contrast lesions. The detection of lesions depends on the inherent difference in contrast between lesions and surrounding normal tissues. The tissue or media present around a resonating nucleus have differential effects that can alter the T1 and T2 relaxation times. However, in general, organic substances such as those found in the body (tissues, organs) have a fairly uniform effect on relaxation times, largely due to the high percentage of water. MRI scans of a substance take advantage of relaxation times (T1 and T2) differences to generate an image of the object being scanned in "slices." The difference in relaxation times of, say, different organs in the body allows a visible image to be formed. However, the largely uniform effect on relaxation times of most parts of the body causes an image that is very difficult to see due to lack of contrast, hence the need for "contrast agents."

Inherent tissue contrast in MRI is determined by differences in:
1) inherent spin density;
2) longitudinal relaxation time (T1);
3) transverse relaxation time (T2); and
4) flow.

Contrast agents can improve visualization of low contrast organs and lesions. The most promising agents affect signal by enhancing relaxation. A contrast agent is a substance, either 1) a paramagnetic metal ion, 2) free oxygen, or 3) a substance with free radicals (unpaired electrons), that has a far different effect on proton relaxivity than water. A good contrast agent can be either directly injected into the target area or tagged to an antibody against the target area (e.g., a cancerous tumor) and thus provide sharp contrast for aid in viewing the area by MRI.

Pharmacologic basis for relaxation enhancement is based on positive magnetic susceptibility (Bourdreaux, E. A. and Mulap, L. N.: THEORY AND APPLICATION OF MOLECULAR PARAMAGNETISM, New York, 1976, John Wiley and Sons). When a substance is placed in an external magnetic field, induced magnetization in the substance is additive to that of the applied field. The magnetic susceptibility of a substance is defined as the ratio of induced magnetization to that of the applied field. Substances can be categorized by their magnetic susceptibility (see Table I).

TABLE I (David Stark and William Bradley: MAGNETIC RESONANCE IMAGING, St. Louis, 1988, Mosby)

| CLASS | BASIS | SUSCEPTIBILITY |
|---|---|---|
| Diamagnetic | paired electrons-no permanent spin moment | $-10^{-6}$ |
| Paramagnetic | unpaired electrons non-interacting permanent moments | $+10^{-1}$ |
| Superparamagnetic | unpaired electrons-non-interacting domains | $+10^{+2}$ |
| Ferromagnetic | unpaired electrons-interacting domains | $+10^{+2}$ |

Diamagnetic substances have negative susceptibilities. Most organic and inorganic compounds are diamagnetic and since all atoms experience induced magnetic affects arising from electron orbital motion, a diamagnetic component is present in all materials. Diamagnetic effects are very weak and can be overwhelmed in magnitude by relatively few unpaired electron spins. Diamagnetic materials are generally of little interest as contrast agents.

Paramagnetic, superparamagnetic, and ferromagnetic substances are characterized by the predominant magnetic effects of unpaired electron spins which produce positive susceptibilities and positive induced magnetization.

Paramagnetism is characterized by independent action of individual atomic or molecular magnetic moments. Ferromagnetism is characterized by solid phase microscopic volumes or domains in which unpaired electron spins are permanently aligned. Multiple domains in bulk can be isotropic (unmagnetized) or anisotropic (magnetized).

Superparamagnetic materials can be regarded as single domain particles. The susceptibilities per atom or mole of these substances exceed those of corresponding soluble paramagnetic species due to magnetic ordering.

Superparamagnetic and ferromagnetic susceptibilities increase linearly with field strength. Superparamagnetic substances unlike ferromagnetic substances are characterized by restoration of induced magnetization to zero upon removal of the external field.

Paramagnetic enhancement of nuclear relaxation was first described in 1946 by Bloch and co-workers (Bloch, F., Hansen, W. N., and Packard, P.: "The nuclear induction experiment", *Physiol. Rev.* 70:474–485, 1946) when they demonstrated a convenient practice of shortening the time needed to observe water $^1$H T1 by adding ferric nitrate (a paramagnetic solute).

Positive susceptibility is necessary, but not sufficient, for effective relaxation. The magnitude of relaxation enhancement also depends on proximity and on correlation time. A mathematical formulation of paramagnetic enhanced solvent relaxation is described by Bloembergen (Bloembergen, N.: "Proton relaxation times in paramagnetic solutions", *J. Chem. Phys.* 27:572, 1957). These equations imply that nuclear relaxation results from several simultaneous mechanisms.

The paramagnetic contribution to nuclear relaxation is proportional to
1) the paramagnetic concentration;
2) the distance ($\gamma^{-6}$); and
3) a time constant describing the dynamic nature of electron-proton interactions (correlation time).

The correlation time is dominated by the fastest rate of paramagnetic tumbling, electron spin flips, or chemical exchange. Due to more optimal correlation of spin motion, nuclear T1 relaxation enhancement in biologic systems is more effective with relaxation agents if large molecular weight or asymmetric shape, that is, relatively long rotational correlation times.

Solvent relaxation is the presence of superparamagnetic particles chiefly differs from that in the presence of paramagnetic solutes due to much greater weighting of the magnetic moment contribution. Compared with paramagnetic solutes, superparamagnetic particulates have
1) increased effective magnetic moment;
2) decreased freedom of molecular motion; and
3) decreased water $^1$H exchange.

The much greater effective magnetic moment dominates these factors and results in T2 shortening caused by long range effect from magnetic field heterogeneity.

The imaging of internal structures and organs of live animals has been an important aspect of medicine since the advent of X-ray usage for this purpose. Among the techniques more recently developed for such imaging are those involving scanning for emission of particles form an internally located radioisotope. Such radioisotopes preferably emit gamma particles and are generally isotopes of metallic elements. One problem common to the diagnostic usage of such gamma particle-emitting radioisotopes concerns the localization of these materials at sites of particular interest rather than to have them randomly dispersed or rapidly excreted, by the kidney, for example. Another problem of such radioisotope mediated imaging concerns optimizing the circulating half-life of radioisotopes, for example, by preventing or accentuating their binding to serum proteins (e.g., albumin), or by prior conjugation (complexation) to polymeric carriers or receptor-binding substances.

A second class of internal body imaging which is undergoing a rapid growth in clinical use is ultrasound imaging. This is based on the detection of differences in the internal velocity (reflectivity) of directed, high-frequency sound waves. Differences in image brightness are produced at the interfaces between tissues with different native densities and ultrasound reflectivities. A present clinical problem is the difficulty of visualizing lesions in the stomach, small and large bowel, bladder, and cavities of the female reproductive tract, due to similarities of ultrasound velocity between these organs of interest and immediately adjacent tissues. Diagnostic introduction of a dense, nonradioactive metal element or ion at sufficient concentrations can confer the significant differences in ultrasound reflectivity which are required to visualize otherwise undetectable tumors and inflammatory lesions.

NMR intensity and relaxation images have been shown in recent years to provide a third important method of imaging internal structures and organs of live animals. Clinical magnetic resonance Imaging (MRI) is a rapidly growing, new form of brain and body imaging. Low-field (proton) MRI detects chemical parameters in the immediate environment around the protons because of body tissues (predominantly water protons because of their relative abundance). Changes in these parameters occur very early in disease and are independent of physical densities detected by ionizing radiation. In the brain and central nervous system, MRI has allowed detection of tumors at an earlier clinical stage and with fewer imaging artifacts than is possible with computerized axial tomography (CAT) (Runge et al., (1983) Am. J. Radiol. V 141, p 1209). Under optimal conditions, image resolution is in the submillimeter size range.

Seven factors are among those making it important to develop nontoxic MRI image-enhancing agents analogous to those available for CAT.
1. They increase the specificity of MRI diagnosis.
2. Smaller lesions can be identified earlier.
3. Image-enhancing agents enhance tumor masses differently than surrounding edema fluid or abscesses. This allows the extent and invasion of tumor to be defined more precisely. Lesion with infiltrative-type growth (e.g., certain metastatic carcinomas and glioblastomas) will require contrast agents for demarcation between tumor and edema fluid (Felix et al. (1985) Proc. Soc. Mag. Res. Med. V 2, p 831).
4. Image-enhancing agents improve the distinction between recurrent tumor and fibrous tissue resulting from surgery and radiation.
5. Image-enhancing agents can decrease the time required per scan and potentially decrease the number of scans required per procedure. This increases the volume of procedures and decreases their expense.
6. Body imaging has a significantly lower resolution (typically 0.5–1.0 cm) and sensitivity (decreased signal-to-noise ratio) than brain imaging (Wesbey et al. (1983) Radiology V 149, p 175). These differences result from the greater inhomogeneity of the magnetic field; the larger radio frequency coil; unequal phase-pulsing of deep versus shallow nuclei; and motion artifacts produced by respiration, cardiac systole, gastrointestinal peristalsis, and voluntary muscle movement; and
7. Advanced (polymeric and microsphere) forms of contrast agents (see below) appear to be required for the optimal acquisition and interpretation of blood-flow and tissue-perfusion images and related spectral (phase) information.

The discrete intensities of a two-dimensional, Fourier-transformed image are described by the following general equation (for spin-echo pulse sequences):

$$\text{Intensity} = N(H) \cdot f(v) \cdot \exp(-TE/T2) \cdot (1 - \exp(TE-TR)/T1),$$

where
$N(H)$ = number of protons in the discrete tissue volume (spin density);
$f(v)$ = a function of proton velocity and the fraction of protons which are moving (e.g., due to following blood);
$TE$ = time between the radio frequency (rf) pulse and the detection of signal (spin-echo);
$TR$ = the interval between repetition of the rf pulse;
$T1$ = the time interval associated with the rate of proton energy transfer to the surrounding chemical environment (spin-lattice relaxation);
$T2$ = the time interval associated with the rate of proton energy transfer, one to other (spin-spin relaxation).

The T1 and T2 times have reciprocal effects on image intensity. Intensity is increased by either shortening the T1 or lengthening the T2 or vice versa depending upon whether proton density, T1-weighted or T2-weighted images are desired. Tissue contrast occurs naturally and is related to variations in the chemical environments around water protons (major contributor) and lipid protons (usually minor). Chemical agents have been used to enhance this natural contrast. The one most widely tested clinically is the paramagnetic metal ion, gadolinium ($Gd^{+3}$) chelated to an appropriate organic chelate (Runge et al. (1983) Am. J. Radiol. V 142, p 619). Although gadolinium shortens both the T1 and T2 times, at the lower does used for clinical imaging, the T1 effect generally predominates and the image becomes brighter. Also, the rf pulse sequence can be programmed to accentuate T1 changes and diminish those due to T2 (Runge et al. (9183) Am. J. Radiol. V 141, p 1209). Hence, "T1-weighted" enhancement can be achieved by selecting the most favorable Gd dose and rf pulse sequence.

The shortening of proton relaxation times by Gd is mediated by dipole-dipole interactions between its unpaired electrons and adjacent water protons. The effectiveness of Gd's magnetic dipole drops off very rapidly as a function of its distance form these protons (as the sixth power of the radius) (Brown (1985) Mag. Res. Imag. V 3, p 3). Consequently, the only protons which are relaxed efficiently are those able to enter Gd's first or second coordination spheres during the interval between the rf pulse an signal detection. This ranges from $10^5$ to $10^6$ protons/second (Brown (1985) Mag. Res. Imag. V 3, p 3). Still, because Gd has the largest number of unpaired electrons (seven) in its 4f orbital, it has the largest paramagnetic dipole (7.9 Bohr magnetons) and exhibits the greatest paramagnetic relaxivity of any element (Runge et al. (1983) Am. J. Radiol. V 141, p 1209 and Weinman et al. (1984) Am. J. Radiol. V 142, p 619). Hence, Gd has the highest potential of any element for enhancing images. However, the free form of Gd is quite toxic. This results in part from precipitation at body pH (as the hydroxide). In order to increase solubility and decrease toxicity, Gd has been chemically chelated by small organic molecules. To date, the chelator most satisfactory from the standpoints of general utility, activity, and toxicity is diethylenetriamine pentaacetic acid (DTPA) (Runge et al. (1983) Am. J. Retail V 141, p 1209 and Weinman et al. (1984) Am. J. Retail V 142, p 619). The first formulation of this chelate to undergo extensive clinical testing was developed by Schering Ag - Berlex Imaging according to a patent application filed in West Germany by Gries, Rosenberg and Weinmann (DE-OS 3129906 A 1 (1981). It consists of Gd-DTPA which is neutralized and stabilized with the organic base, N-methyl-D-glucamine (meglumine). The Schering-Berlex agent is nearing completion of Phase III clinical testing at selected centers across the United States and abroad. The results of preliminary studies indicated that almost all human brain tumors undergo significant enhancement (Felix et al. (1985) Proc. Soc. Mag. Res. Med. V 2, p 831 and K. Maravilla, personal communication). These include metastatic carcinomas, meningiomas, gliomas, adenomas and neuromas. Renal tumors are also enhanced satisfactorily (Lanaido et al. (1985) Proc. Soc. Mag. Res. Med. V 2, p 877 and Brasch et al. (183) Am. J. Retail. V 141. p 1019). The Schering-Berlex formulation was available for general clinical use by 1989.

Despite its satisfactory relaxivity and toxicity, this formulation has four major disadvantages.

(1) Chelation of Gd markedly decreases its relaxivity (by ½ an order of magnitude). This happens because chelators occupy almost all of Gd's inner coordination sites which coincide with the strongest portion of the paramagnetic dipole (Koenig 1985) Proc. Soc. Mag. Res. Med. V 2, p 833 and Geraldes et al. (1985) Proc. Soc. Mag. Res. med. V 2, p 860).

(2) Gd-DTPA dimeglumine, like all small paramagnetic metal chelates, suffers a marked decrease in relaxivity at the higher radio frequencies used clinically for proton imaging (typically 5 MHz, 2T) (Geraldes et al. (1985) Proc. Soc. Mag. Res. med. V 2, p 860).

(3) Due to its low molecular weight, Gd-DTPA dimeglumine is cleared very rapidly from the bloodstream (t½ in 20 minutes) and also from tissue lesions (tumors) (Weinman et al. (1984) Am. J. Radiol V 142, p 619). This limits the imaging window (to ca. 30 to 45 minutes); limits the number of optimal images after each injection (to ca. 2); and increases the agent's required dose and relative toxicity.

(4) The biodistribution of Gd-DPTA is suboptimal for imaging of body (versus brain) tumors and infections. This is due to its small molecular size. Intravenously administered Gd-DTPA exchanges rapidly into the extracellular water of normal tissues, as well as concentrates in tumors and infections. This is facilitated by an absence in body organs, of the "blood-brain" vascular barrier which partly restricts the exchange of Gd-DTPA into the extracellular water of normal (versus diseased) brain. The result in body organs, is a reduced difference in the concentration of Gd-DTPA between normal and diseased regions of tissue, and hence, reduced image contrast between the normal and diseased regions of the organ. Also a disproportionate quantity (>90%) of Gd-DTPA is sequestered very rapidly in the kidneys (Weinman et al. (1984) Am. J. Radiol V 142, p 619). Of much greater interest to body MRI, are the abdominal sites involved in the early detection and staging of tumors (particularly the liver, and also the spleen, bone marrow, colon and pancreas).

Three approaches have been taken in attempts to overcome these disadvantages.

(1) Alternative, small chelating molecules have been tested. These make Gd more accessible to water protons but still chelate the metal with a sufficient affinity to potentially control its toxicity in vivo. The most effective of these chelators is DOTA, the poly-azamacrocyclic ligand, 1,4,7,10-tetraazacyclododecane-N,N',N''-tetraacetic acid (Geraldes et al. (1985) Proc. Soc. Mag. Res. Med. V 2, p 860). Its relaxivity is approximately 2 times greater than that of Gd-DTPA over a wide range of Larmor frequencies. However, it is still less active than free Gd.

(2) Gd and Gd-chelates have been chemically conjugated to macromolecules, primarily the proteins, albumin (Bulman et al. (1981) Health Physics V 40, p 228 and Lauffer et al. (1985) Mag. Res. Imaging V 3, p 11), asialofetuin (Bulman et al. (1981) Health Physics V 40, p 228), and immunoglobulins (Lauffer et al. (1985) Mag. Res. Imaging V 3, p 11 and Brady et al. (1983) Soc. Mag. Res., 2nd Ann. Mtg., Works in Progress, San Francisco, Calif.). This increases the relaxivity of Gd by slowing its rate of molecular tumbling (rotational correlation time) (Lauffer et al. (1985) Mag. Res. Imaging V 3, p 11). This improves coupling of the energy-transfer process between protons and Gd (Geraldes et al. (1985) Proc. Soc. Mag. Res. Med. V 2, p 860, Lauffer et al. 91985) Mag. Res. Imaging V 3, p 11 and Brown et al. (1977) Biochemistry V 16, p 3883). Relaxivities are increased by multiples of 5 to 10 relative to Gd-DTPA (when compared as $R1 = 1/T1$ values at 1 millimolar concentrations of Gd) and by multiples of 2.5 to 5.0 (when compared as the molarities of Gd required to produce a specified decrease in the T1 relative to a control solution (physiologic saline).

The reasons for using the latter method of comparison are that 1) millimolar concentrations of Gd are never achieved in vivo—actual tissue concentrations achieved in the usual image enhancement are between 20 and 100 micromolar Gd; 2) the slopes of R1 graphs are frequently nonparallel for different enhancing agents; 3) the second method allows agents to be compared according to the more customary means of chemical activity ratio, in other words, as the concentration required to produce a specified percentage decrease in the T1 (or T2) relaxation time. The second method is considered preferable. A drawback of conjugating DTPA to protein carriers for use in NMR image enhancement is that it has been difficult to stably conjugate more than 5 DTPAs (and hence Gd's) to each albumin molecule (Bulman et al. (1981) Health Physics V 40, p 228, Lauffer et al. (1985) Mag. Res. Imaging V 3, p 11 and Hnatowioh et al. (1982) Int. J. Appl. Radiat. Isot. V 33, p 327 (1982).

Comparably low substitution ratios (normalized for molecular weight) have been reported for immunoglobulins (Lauffer et al. (1985) Mag. Res. Imaging V 3, p 11 and Brady et al. (1983) Soc. Mag. Res., 2nd Ann. Mtg., Works in Progress, San Francisco, Calif.) and fibrinogen (Layne et al. (1982) J. Nucl. Med. V 23, p 627). This results from the relative difficulty of forming amide bonds, the comparatively low number of exposed amino groups on typical proteins which are available for coupling, and the relatively rapid hydrolysis of DTPA anhydride coupling substrate which occurs in the aqueous solvents required to minimize protein denaturation during conjugation (Hnatowich et al. (1982) Int. J. Appl. Radiat. Isot. V 33, p 327 (1982) and Krejcarek et al. (1977) Biochem. Biophys. Res. Comm. V 77, p 581). The overall effect of these suboptimal conditions is that a very large dose of carrier material is required to achieve significant in vivo effects on MR images. At this high dose, the carrier produces an unacceptable acute expansion of the recipient's blood volume by an osmotic mechanism. Indeed, low substitution ratios have generally limited the use of such protein-chelator-metal complexes to the more sensitive (low-dose), radiopharmaceutical applications (Layne et al. (1982) J. Nucl. Med. V 23, p 627).

An attempt to overcome this low substitution ratio has been made by conjugating DTPA to the non-protein carrier, cellulose (Bulman et al. (1981) Health Physics V 40, p 228), however the chemical method employed results in continued suboptimal substitution of DTPA to carrier, the nonbiodegradability of cellulose and its water-soluble derivatives and the reported molecular aggregation which results from organic-solvent conjugation (in dimethylformamide) of CNBr-activated cellulose to the diaminohexyl spacer groups which link the carrier to DTPA, have rendered this class of carrier-conjugates unacceptable for intravenous administration at the doses required for MR image enhancement.

A very important consideration in the image enhancement of solid tumors and inflammatory lesions by polymeric contrast agents is that, in order for these agents to extravasate (exit) efficiently from the microcirculation into adjacent diseased tissues, they must be completely soluble—e.g., not be contaminated by intermolecular or supramolecular microaggregates. Optimal tumor access and localization requires that the molecular size of such agents generally be less than approximately 2,000,000 daltons (ca. 2 to 3 nanometers in molecular diameter), and preferably less than 500,000 daltons (ca. 0.5 to 1.0 nanometers in molecular diameter) (Jain (1985) Biotechnology Progress V 1, p 81). For this reason, with rare exceptions the particulate and microaggregate classes of contrast agents (which comprise the liposomes, colloids, emulsions, particles, microspheres and microaggregates, as described below) do not concentrate efficiently in most solid tumors or inflammatory lesions. Instead, following intravenous administration, these supramolecular-sized agents: a) are first circulated in the bloodstream for relatively short intervals (225 minutes to 24 hours, depending on size), potentially allowing direct image enhancement of the blood pool (plasma compartment); and b) are subsequently cleared by specialized (phagocytic) cells of the reticuloendothelial tissues (liver, spleen and bone marrow), potentially allowing selective enhancement of these normal tissues, but producing indirect (negative) enhancement of lesions within these tissues (due to exclusion of the agents from the diseased regions). Additionally, following installation into the gastrointestinal tract and other body cavities, these particulate and microaggregate classes of agents can produce direct image enhancement of the fluid within these cavities, and thereby potentially delineate mass lesions which encroach upon the lumens and cavities. Both microspheres and microaggregates are supramolecular in size. The microaggregate class of agents is produced (intentionally or unintentionally) by either a) molecular cross-linking of individual polymer molecules or b) secondary aggregation of previously single (soluble) polymers, as induce by charge attraction or hydrophobic bonding mechanisms. It is distinguished from the microsphere class of agents by virtue of its smaller particle size, which ranges from approximately 2,000,000 daltons (ca. 2 to nanometers in diameter) to 0.1 micrometers (=100 nanometers in diameter). It is important to note that microaggregates are cleared by reticuloendothelial phagocytes with significantly less efficiency and rapidity than are microspheres. In general, this property makes microaggregates a less preferred class of agents for visualizing the liver, spleen and bone marrow under the usual conditions of clinical imaging, for which prompt post-injection contrast enhancement is required.

(3) Gd-DTPA has been entrapped in liposomes (Buonocore et al. (1985) Proc. Soc. mag. Res. med. V 2, p 838) in order to selectively enhance images of the reticuloendothelial organs (liver, spleen and bone marrow) and potentially the lungs. Liver clearance is mediated by phagocytic (Kupffer) cells which spontaneously remove these small (0.05 to 0.1 um) particles from the bloodstream (Buonocore et al. (1985) Proc. Soc. Mag. Res. Med. V 2, p 838). (Particles larger than 3 to 5 um are selectively localized in the lungs due to embolic entrapment in lung capillaries.) A recent report indicates that the small-sized Gd-liposomes produce effective decrease in liever T1's (as determined spectroscopically without imaging) (Buonocore et al. (1985) Proc. Soc. Mag. Res. med. V 2, 0838). Also, insoluble GdDTPA colloids have recently been reported to enhance MR images of rabbit livers under in vivo conditions (Wolf et al. (1984) Radiographics V 4, p 66). However, three major problems appear to limit the diagnostic utility of these devices. The multilamellar, lipid envelopes of liposomes appear to impede the free diffusion of water protons into the central, hydrophobic cores of these carriers, as assessed by the higher does of Gd required for in vitro relaxivities equivalent to Gd-DTPA dimeqlumine (Buonocore et al. (1985) Proc. Soc. mag. Res. med. V 2, p 838). This increases the relative toxicity of each Gd atom.

Even more importantly, these same lipid components cause the carriers to interact with cell membranes of the target organs in a way which leads to a marked prolongation of tissue retention (with clearance times of up to several months) (Graybill et al. (1982) J. Infect. Dis. V 145, p 748 and Taylor et al., 1982 Am. Rev. Resp. Dis. V 125, p 610). Two adverse consequences result. First, image enhancement does not return to baseline in a timely fashion. This precludes re-imaging at the short intervals (ca. 1 to 3 weeks) needed to assess acute disease progression and treatment effects. Second, significant quantities of the liposomally entrapped Gd-DTPA may be transferred directly into the membranes of host cells (Blank et al. (1980) Health Physics V 39, 913; Chan et al. (1985) Proc. Soc. Mag. Res. Med. V 2, p 846). This can markedly increase the cellular retention and toxicity of such liposomal agents. The consequences for Gd toxicity have not yet been reported. Protein (albumin) microspheres with entrapped Gd and Gd chelates have been prepared and determined (Saini et al. (1985) Proc. Soc. Mag. Res. Med. V 2, p 896) to have only modest effects on T1 relaxivity in vitro. This is because most of the Gd as well as other entrapment materials (Widder et al. (1980) Cancer Res. V 40, p 3512) are initially sequestered in the interior of these spheres and are released very slowly as the spheres become hydrated (with t½'s of hours) (Widder et al. (1980) Cancer Res. V 40, 3512).

Emulsions of insoluble gadolinium oxide particles have been injected into experimental animals with significant image-enhancing effects on the liver (Burnett et al. (1985) Magnetic Res. Imaging V 3, p 65). However, these particles are considerably more toxic than any of the preceding materials and are thus inappropriate for human use. Because of the significant disadvantages of existing MR image contrast agents, the present applicant has formulated improved, second-generation prototype agents with reduced toxicity, phenominally increased effectiveness potentially increased selectivity of tumor and organ uptake, as well as a significant potential for enhancing blood flow images.

Many of the advantages shown for the present developments concerning NMR image-enhancing agents (also referred to herein as NMR contrast agents or MR (magnetic resonance) contrast agents) are also expandable to other areas. Gadolinium and related agents can produce characteristic changes in the NMR spectrum of adjacent NMR-susceptible nuclei. These changes include: modulation of resonance peak positions, widths, intensities, and relaxation rates (which affect intensity). Hence, perturbation of spectra by such chemical shift-relaxation agents can be used to localize and identify the source of NMR signal with respect to organ location, tissue compartment (intravascular versus extravascular), cell type within the tissue, and potentially, the specific metabolic pathways within cells which are altered by drugs and disease. Also in certain situations, ultrasound imaging or body scanning of radioisotopic emissions is particularly useful in achieving insight into internal structures. The radioisotopic emissions most frequency scanned are those of metallic radioisotopes emitting gamma particles, however, positron emission tomography is experiencing increased clinical use. The molecular formulation and mode of administering these radioisotopic metals will have significant consequences on the internal localization and body half-life of these radioisotopes, potentially leading to increased diagnostic usage of these ultrasound images and emission scannings.

The present invention includes an image-enhancing or spectral-shift agent comprising a biodegradable, water-soluble or insoluble melanin polymer, synthetic or derived from natural sources and having a signal-inducing metal or metal particle incorporated therein.

Melanins are a group of pigments derived from several different amino acid substrates in the natural world. Different types of melanins are responsible for much of the coloration in animals, plants, and bacteria. Melanins are usually classified in one of three groups: eumelanins, such as those found in hair, skin, feathers, and as a part of the coloration in reptiles and fish; phaeomelanins, which produce human red hair and the read fur of foxes; and allomelanins, which are most often present in bacteria and plants. An example of one of the most striking effects of a combination of eumelanins and phaeomelanins in the patterns found in the plumage of certain tropical birds.

Melanins are created by the action of enzymes on any of several amino acid precursors. For example, tyrosine is the precursor of most eumelanins. However, the exact process by which an amino acid is converted to melanin is unknown, and indeed, seems to vary from one pigment to another even when formed from the same substrate. In general, black pigments are formed from precursors including 3,4-dihydroxyphenylalanine (DOPA), catechol, and various other dihydroxy- substances.

| OH | CH | COOH | OH | |
|----|----|------|----|----|
|    | CH |      |    |    |
| OH |    | NH   | OH | NH |
| 3,4-dihydroxyphenylalanine (DOPA) | | | 5,6-dihydroxyindole | |
| HO |    |      | OH | OH |
| OH |    |      |    |    |
| catechol | | | 1,8-dihydroxynaphthalene | |

These substances have many active centers for polymerization. Compounds with fewer active centers are precursors to melanins of brown, reddish-brown, or yellow-brown color.

Melanins in pure form are usually insoluble in water as well as in most organic solvents, making them difficult to work with. In part due to this, not all of the chemical properties of melanins have been identified. However, recent studies using electron spin spectroscopy have identified free-radical properties of melanin.

Synthetic melanins can be created from most of the precursors used in nature by using almost any chemical oxidant or free-radical polymerizer, or, in some cases, merely leaving dissolved substrate open to the air overnight.

SUMMARY OF THE INVENTION

The present invention involves an image-enhancing agent comprising melanin or melanin combined with a non-dissociable signal-inducing metal. In one embodiment the agent preferably contains at least about 0.1 micromole metal per gram but can vary greatly depending upon the synthetic conditions employed to produce the agent.

In reference to the melanin-metal combination of the present invention, the signal-inducing metal has an association constant for its melanin combination of at least about $10^{20}$, i.e., it is virtually non-dissociable. Upon suspension or dissolution in water the metal remains undissociated for an indefinite period. A preferred signal-inducing metal is paramagnetic or superparamagnetic, of course for magnetic resonance imaging. A preferred paramagnetic or superparamagnetic metals are gadolinium, iron, nickel, copper, erbium, europium, praseodymium, dysprosium, holmium, chromium or manganese. Gadolinium is a preferred metal. In one aspect, melanin free of added metal of any kind affects proton relaxivity more effectively than Gd-DTPA.

The metal is incorporated into the melanin in an ionic, uncharged, or particulate form. Metals may be utilized which are particularly useful to modify ultrasound images by the enhancement of the image obtained from emission and detection of high-frequency soundwaves. Metals emitting gamma particles may also be utilized to enhance images resulting from gamma particle emission scanning. $^{51}$Chromium, $^{68}$gallium, $^{99m}$technetium and $^{111}$indium are preferred metals for gamma particle scanning.

The best image-enhancing agents of the present invention have preferred molecular weights between about 1,000 daltons and about 100,000 daltons, although even larger molecular weights may be appropriate for particular uses. This agent may also utilize melanin of the form phaeomelanin, eumelanin or allomelanin, each depending on the particular melanin precursors utilized for melanin synthesis in the presence of a signal inducing metal.

To enhance the water solubility of the agents of the present invention, they may be affixed to water-solubilizing agents such as organic amines or acids. A preferred organic amine is N-methylglucamine or triethylamine and a preferred acid is glutamic acid. The melanin or melanin-signal-inducing metal combination of the present invention may additionally be attached to biological site-directing moieties such as proteins, peptides or antibodies having binding specificity for particular biological sites of interest.

Of course, a method of preparing the above image enhancing agents of the present invention constitutes an important part of this invention disclosure. Such methods involve forming melanin from melanin precursors in the presence of levels of signal inducing metals sufficient to form a melanin signal-inducing metal combination having levels of metal sufficient to enhance desired images. Melanin precursors generally are those comprising a hydroxyphenyl or dihydroxyphenyl moiety. These melanin precursors include, but are not limited to hydroxyphenylalanine, catechol, dopamine, tyrosine, 5,6-dihydroxyindole, 5,6-dihydroxyindole-2-carboxylic acid, 5,6-dopachrome, 5,6-indolequinone, dopaquinone, 3-aminotyrosine, and dihydroxyphenylethylamine, each of which may be alone, or in combination, or mixed with a thiol-containing substance such as glutathione or cysteine. The formation of melanin from these precursors is induced by an oxidizing or free radical-generating agent. Free radical-generating agents are preferably azo compounds, persulfates or peroxides. Preferred free radical-generating or oxidizing agents include but are not limited to ammonium persulfate, azobisisobutyronitrile, hydrogen peroxide, oxygen, sodium nitrite, benzoylperoxide and t-butylhydroperoxide. Melanin is also formed by the action of certain enzymes on appropriate substrate melanin precursors. It is believed that such enzymes may be utilized to incorporate signal-inducing metals in melanin by allowing the enzymatic catalysis of melanin precursors to proceed in the presence of metal ions. Although metal ions may inhibit certain of these enzymes under some conditions, it is believed that conditions may be readily determined where such inhibition is not critical to melanin-signal-inducing metal combinations and formations. One such enzyme is polyphenol oxidase and another is tyrosinase.

The present invention naturally includes methods of imaging which utilize melanin or the melanin-signal-inducing metal combination of the present invention. Such methods include magnetic resonance imaging, gamma emission scanning, and ultrasound imaging, for example. Administration of an agent of the present invention in an appropriate manner such as parenteral, intravascular, enteral or other methods prior to the imaging itself will enhance such imaging so that more accurate images will be obtained.

BRIEF DESCRIPTION OF THE DRAWINGS

FIG. 8 illustrates the effect upon $T_1$ relaxation rate versus concentration of superparamagnetic iron-melanin.

FIGS. 9–12 illustrate the effect of (L-DOPA) melanin-Gd upon $T_1$ relaxation rate versus concentration of gadolinium for four different molecular weight ranges.

FIGS. 14A and 14B show the MRI images obtained respectively without or with melanin-Gd injected into the circulatory system.

DESCRIPTION OF PREFERRED EMBODIMENTS

Figure 2:
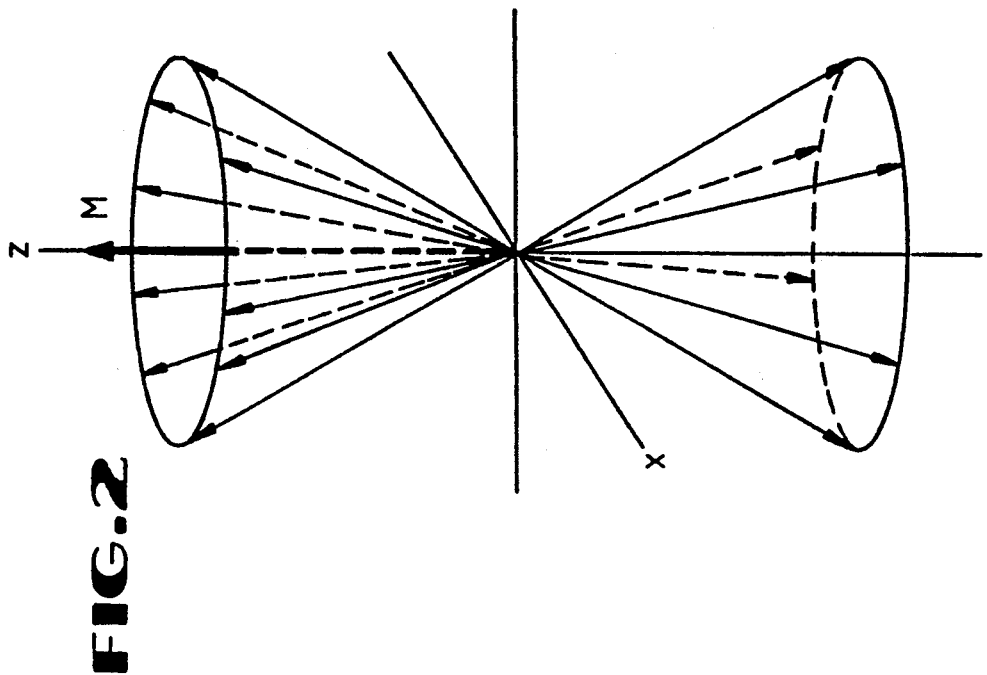
FIG. 2 illustrates macroscopic magnetization where nuclei are in a low spin state absent any outside influence.
Figure 1:
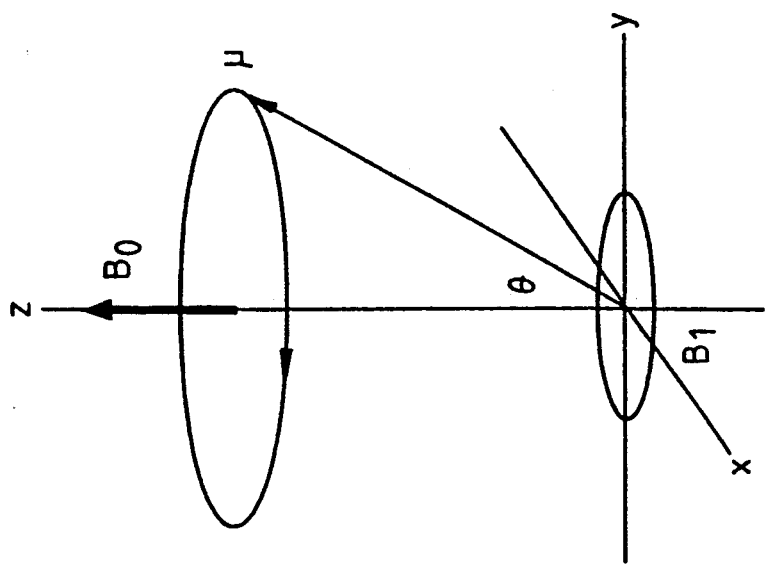
FIG. 1 illustrates a magnetic moment shown as revolving around a fixed magnetic field at a fixed frequency.
Figure 5:
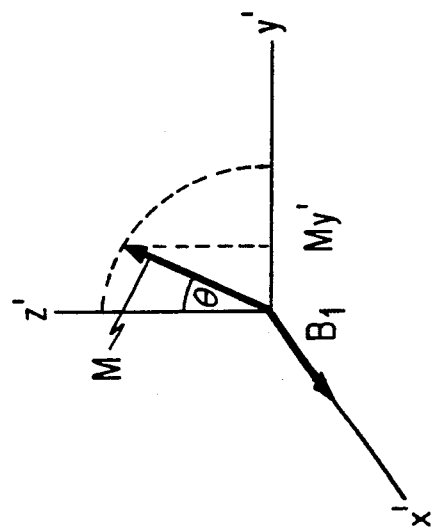
FIG. 5 illustrates the return of M components to their original values after a time ($T_2$).
Figure 4:
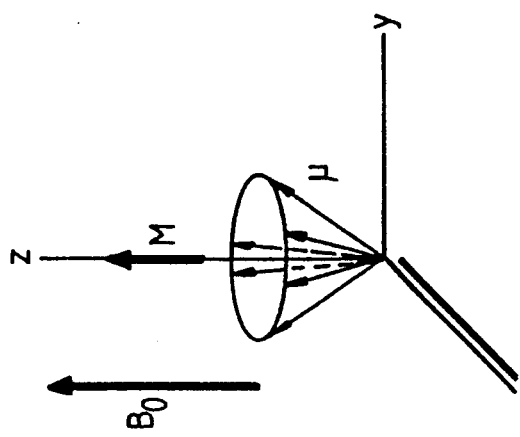
FIG. 4 illustrates the return of individual magnetic moments to their original state.
Figure 3:
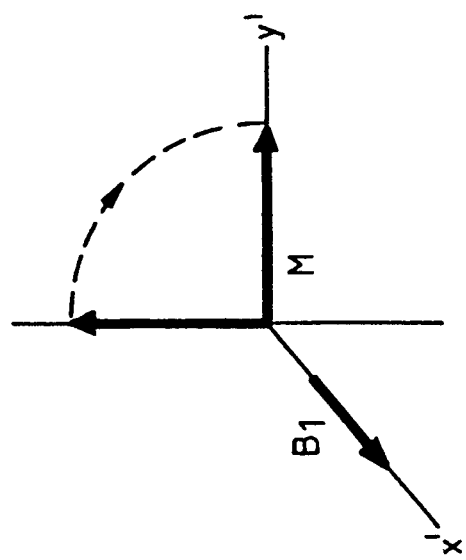
FIG. 3 illustrates the effect of additional magnetic fields being applied to induce M to rotate to the x'y' plane.

The present disclosure discloses the formulation and use of new contrast-enhancing agents particularly useful for magnetic resonance imaging. This new class of image-enhancing agents relates to melanin and combinations of melanin and signal-inducing metal ions. Although other imaging techniques and corresponding metals may be likewise applicable, the primary focus of this invention relates to magnetic resonance imaging and paramagnetic or superparamagnetic metal inclusions in melanin. The relaxation rates, T1 and T2 of nuclei proximate to melanin-paramagnetic metal complexes appear altered to a greater extent than with the more traditional paramagnetic metal-chelator complexes such as gadolinium-DTPA.

This invention primarily involves the synthesis, preparation and use of a class of melanin materials as nuclear magnetic resonance relaxation agents for effective contrast enhancement and/or spectral shifts in magnetic resonance imaging and spectroscopy. This class of new paramagnetic materials shows greater than a 1000-fold increase in the NMR relaxation rate of protons in water over the best readily usable relaxation affecting agent so far known (gadolinium - DTPA chelate). This observation has great potential importance in contrast enhancement for magnetic resonance imaging since contrast agents are becoming more necessary to differentiate between iso-intense regions of normal and diseased tissue. It is also noted herein that melanin alone may have a greater relaxivity effect than the current field standard, Gd-DTPA-Gd complexes.

Furthermore, these melanin contrast agents may even be affixed to monoclonal antibodies or to other target (site) specific biochemical agents enabling site-directed MR imaging biochemical agents that would provide site-directed MR imaging and spectroscopy. This goal of site-specific imaging agents has not before been completely successful because, for example, antibodies normally function at nanomolar concentrations and the minimum concentrations of contrast agents, where effects on relaxation properties can be seen, are millimolar. The melanin-based agents of the present invention containing gadolinium and superparamagnetic iron, function in a micromolar concentration range which is much closer to the physiologic range of antibody action.

By incorporating other metals, a whole class of contrast agents with different properties is accessible. Likewise, the degree of polymerization of the melanin can be synthetically controlled producing a molecular weight range of agents that have quite different potential applications (e.g., blood pool, oral contrast). Alternatively, the effectiveness of the agent can be adjusted by the amount of gadolinium (or other metal) that is synthetically incorporated in the agent. Also chemical derivatization of the melanin-metal compounds could provide a lipophilic agent for permeation of the blood-brain barrier or other agents attached to alternative types of site-specific materials (liposomes, peptides, enzymes, etc.). The choice of alternative melanin precursors and/or various reaction conditions including catalysts and reaction times may be manipulated to produce products having a wide variety of clinical and physical properties for obtaining image-enhancing agents having numerous biological distribution and other properties.

Finally, the use of these materials to produce in vivo high resolution NMR chemical shift changes is a largely unexplored research area. Lanthanide metal complexes have been employed routinely for chemical shift alterations in in vitro high resolution NMR for the purposes of quantitation and identification; consequently, these new melanin-materials have opened an entirely new area of in vivo magnetic resonance imaging and spectroscopic applications.

The primary purpose and use of this invention is to alter the nuclear magnetic resonance (NMR) relaxation rates, T1 and T2, of protons or other nuclei that are proximate to the melanin material. If the T1/T2 relaxation rates of the observed nuclei are changed relative to an adjacent unaffected region, then the magnetic resonance (MR) image or spectra acquired from that region will show altered contrast or a particular nuclei in the environment of the agent will exhibit an altered chemical shift.

By altering the contrast of a specific region, that area can be visualized, relative to other areas. There are many tissue structures that have such a similar or iso-intense contrast in MR imaging that prevent their easy visual evaluation or prevent the detection of lesions, tumors, or altered tissue structures. By adding this melanin agent, iso-intense regions will become substantially altered allowing more easy detection and identification.

The effect on the chemical shift of specific NMR resonances, due to the paramagnetic effect of the melanin agent, would allow them to be more easily detected, identified, and/or quantitated when the melanin agent alters the microenvironment surrounding the nuclei of interest.

An important purpose and use of this invention is in the construction of specific contrast agents for in vivo MR imaging applications. Employing the melanin matrix, different additives (e.g. metal ions) can be included to alter either the T1 or the T2 or both of a desired organ, tissue, lesion, or structure to enhance its detectability. Furthermore, the melanin matrix can be chemically attached through covalent, ionic, hydrophobic or hydrophilic bonding to mono- or poly-clonal antibodies, receptors, liposomes, membranes, proteins, enzymes, polypeptides, etc. These melanin-containing materials have the potential to be site (target) specific relaxation agents that will allow visualization and/or identification of the target structure. Consequently, disease states and healthy tissue could be non-invasively probed by MRI with enhanced specificity and detectability.

The following aspects of this invention, among others, are novel:

1. Melanin that has gadolinium ions or superparamagnetic iron particles incorporated shows the largest effect on NMR relaxation rates that has ever been reported. Micromolar concentrations (or less) of the melanin agent produce similar effects that present relaxation agents achieve at millimolar concentrations. Incorporation of other metals may provide very specific agents designed for specific applications such as chemical shift alterations using metals of the lanthanide series. Alternatively other paramagnetic metal ions may show relaxation effects superior to the already improved agents containing gadolinium or superparamagnetic iron.

2. Melanin is a natural polymer that can be synthesized from many related materials (e.g. L-DOPA, dopamine, catechol, tyrosine, other dihydroxy aromatics) to produce different polymers that have different metal inclusion and binding characteristics, free radical contents, different molecular weight ranges, etc. These factors will influence the relaxation enhancement parameters; consequently, a melanin agent can be synthetically tailored for specific purposes by using selected melanin precursors, selected metal ions, selected appendant functional groups, and selected synthetic conditions designed to produce, for example, different molecular weight agents.

3 Because the melanin is a polymeric substance, the molecular weight ranges of melanin agents could be tailored to produce an agent of desired size. For example, low molecular weight melanin agents can be synthesized with lipophilic appendant groups for permeation of the blood-brain barrier. Other higher molecular weight agents materials could be used as oral contrast agents or slowly migrating agents that allow observation at injected sites. As the molecular weight increases above 1,000 daltons, there appears to be a synergistic effect on decreasing the relaxation times (T1 and T2) caused by the free radical nature of the melanin polymer when coupled with the metal (e.g., gadolinium) being employed. The high degree of radical delocalization due to extended conjugation in the melanin polymers (e.g., their strong UV/VIS absorption and black color) is possibly responsible for the enhanced relaxation caused by coupling the metal to the melanin through inclusion into the interior of the polymer.

Although melanins are known to act as ion-exchange materials and bind metals on their external surface, these metals are easily removed by exchange or dilution (or dialysis). In fact both L-DOPA-melanins and L-DOPA melanin-gadolinium-polymers bind gadolinium and exhibit decreases in T1 and T2; however, upon dilution the L-DOPA melanin returns to its intrinsically lower effect (inherent free radical context) on T1 or T2 whereas the included gadolinium incorporated during the synthetic protocol returns a high level effect on T1 and T2. Techniques normally used to dissociate metals from chelates do not remove the metals included in the melanin-metal polymers produced according to the present invention.

4. A large number and type of metals can be incorporated into melanin, resulting in different materials that are expected to show equivalent but somewhat different effects that potentially make them very useful. For example, incorporation of superparamagnetic iron creates an agent that affects T2 relaxation extremely strongly (e.g., T2 relaxivity=32,815 (mmole/l)$^{-1}$sec$^{-1}$) while incorporation of gadolinium affects T1 relaxation very strongly (T1 relaxivity=30 (mmole/l)$^{-1}$sec$-1$). Incorporation of europium or praseodymium, two very useful and potent NMR chemical shift effectors, although only showing a moderate T1 relaxivity effect of 19.8 and 18.6 (mmole/l)$^{-1}$sec$^-$, may show enhanced chemical shift changes in vitro as well as providing the first case of an in vivo chemical shift agent for MR spectroscopy.

5. The synthesis of the melanin polymer must be accomplished in the presence of a metal ion that is to be incorporated. Although prepolymerized melanin can be placed in a solution of a metal ion or exchanged into the melanin polymer, the exchange is not very efficient. Contrast agents produced in the latter manner are not as effective as agents polymerized in the presence of a metal and, upon dilution or reaction with amines or azide, lose their effect much more rapidly than metal-containing melanins synthesized in the presence of a metal vide infra.

The addition of a metal ion to melanin (either by de novo synthesis or by exchange) often leads to a precipitation of the melanin complex from aqueous solution. Appropriate treatment with a suitable solubilizer that is biocompatible, e.g. N-methylglucamine, triethylamine or glutamic acid, provides a water soluble salt. Other techniques for enhancing solubilization of melanins include acidification of the polymer to eliminate salts formed during the oxidative polymerization. The melanin free acid, depending upon the monomer used, can be made more soluble in aqueous solution as well as many other organic solutions.

6. Chemical derivatization of the melanin-metal complex is easily accomplished by a variety of well-established reaction protocols. Such derivatization could lead to melanin agents that are highly lipophilic; are attached to a liposome, membrane, receptor protein, enzyme, polypeptide, etc.; or are attached to mono or polyclonal antibodies to be site-specific contrast agents.

7. Although toxicity and tolerance must be specifically evaluated, natural melanin is ubiquitous and it appears that such an agent should be generally well tolerated. Initial data obtained with a rodent model has shown no evidence of acute toxicity. Although the metal ion content of the melanin agents can vary, it is anticipated that any metal employed would not cause acute toxicity because of protection by inclusion into the interior of the melanin polymer and the inability of the metal to dissociate. The melanin agent is at least partially, if not all, excreted in the urine of the rodent model.

Because the melanin agents exhibit such pronounced relaxation effects, they may be the first agents that can be incorporated into monoclonal antibodies and successfully show site specific contrast affects at close to the nanomolar concentrations at which antibodies normally function. This technique would provide a protocol that could replace radionuclide imaging and produce information that is similar to what is obtained from PET (position emission tomography) but would potentially have much higher resolution.

9. Relaxation parameters (T1 and T2) have been measured at three different magnetic field strengths for a melanin-gadolinium agent and showed substantially enhanced T1 and T2 relaxation rates as compared to melanin synthesized without gadolinium ions present. The results indicate that the melanin agent is effective as a contrast agent in the low micromolar concentration range. A melanin agent containing superparamagnetic iron has been prepared which has a T1/T2 effect approximately ten fold greater than the best gadolinium agent. As Tables 1-4 show, a number of metals and melanin polymers show enhanced T1 relaxivity.

Animal tests have shown good tolerance of administered melanin-Gd. Preliminary results indicate the melanin agent is an excellent oral contrast agent when administered in the animals' water. Intravenous injection of the agent was also well tolerated (no acute, observable toxic effects). These preliminary results suggest that the agent is also effective as a blood pool contrast agent. The circulatory system, kidneys, liver, and bladder showed enhancement of contrast. Injection into the rabbit temporomandibular joint (TMJ) has also been accomplished and examined by MRI. Contrast was substantially enhanced at the injection site; however the area around the injection became hard with time and evaluation of these results has not been completed.

Several well recognized synthetic methods can be employed to prepare melanin agents that result in various amounts of different metal ions being incorporated, different molecular weights for the resulting products, and different solubilities of the final products (because of different melanin precursors used), etc. The following represents a typical preparation of a gadolinium containing L-DOPA melanin of approximately 14,000 molecular weight that shows substantially enhanced relaxivity (T1/T2).

The typical chemical reaction involved is:

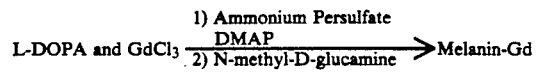

A typical reaction involves mixing 1.25 g L-DOPA, 0.75 dimethyl-aminopyridine (DMAP), 0.25 g GdCl$_3$ and 0.15 g ammonium persulfate in 150 ml water. The reaction is stirred for 30 minutes and 10 g N-methyl-D-glucamine is added and heated at 50° C. overnight. After cooling, the solution of melanin-Gd is dialyzed against a 14,000 MW cutoff (MWCO) dialysis membrane. The resulting aqueous solution can be directly used or concentrated by evaporation.

Figure 6:
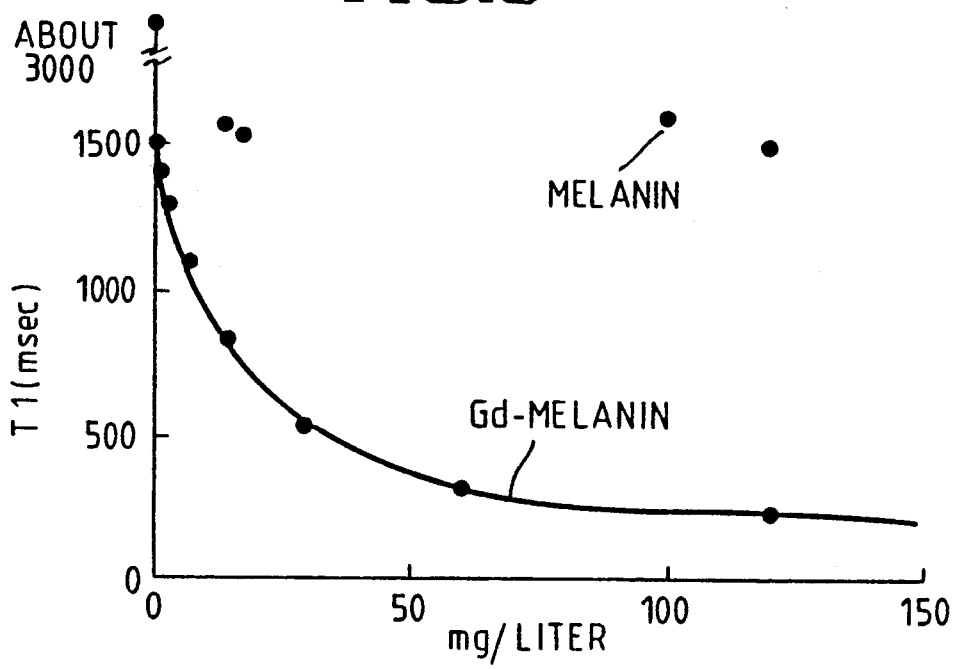
FIG. 6 shows the effectiveness of a Gd-melanin agent of melanin in the absence of gadolinium as having less effect on the $T_1$ relaxation time at high concentration for $T_1$ relaxation time alteration.

The attached graph (FIG. 6) of T1 relaxation rate versus concentration (g/1000 g H$_2$O) of the melanin-Gd agent shows the pronounced effect on the proton T1 of the melanin-Gd solution. Note that native melanin also has a significant effect on T1.

Figure 12A:
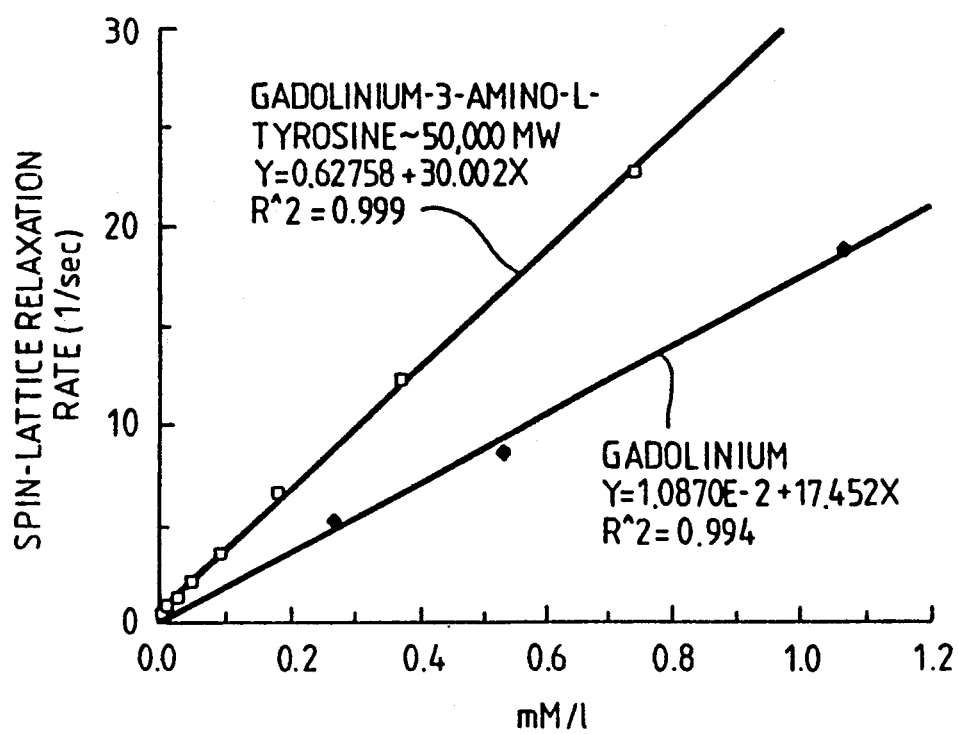
FIG. 12A illustrates the effects upon the T1 relaxation rate of melanin-Gd prepared from 3-amino-L-tyrosine.
Figure 12B:
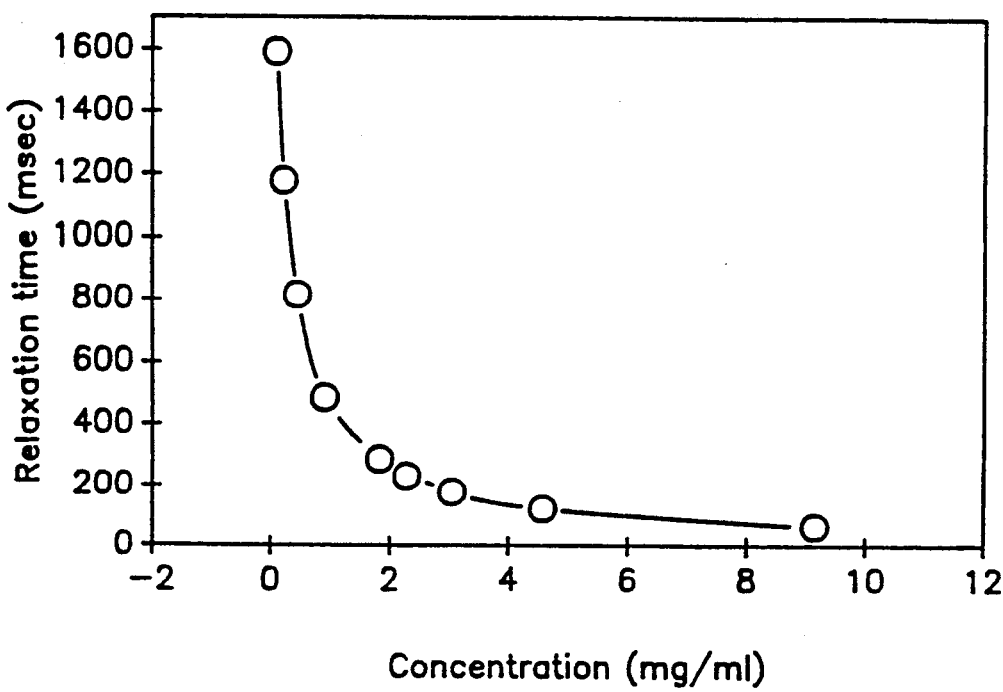
FIG. 12B illustrates the effect of superparamagnetic FeO incorporated into melanin upon relaxation time.

This melanin-Gd material can be further fractionated according to molecular weight. The initial dialysis solution can be evaporated to yield a low molecular weight melanin-Gd. Similar reaction conditions can be used to produce melanin with superparamagnetic iron or other metals. By varying the catalyst, reaction time and temperature, different molecular weight melanins are produced. Furthermore, it is possible to take preformed melanin (either synthetic or natural) and exchange gadolinium or iron into the polymer. There materials; however, show a smaller effect on the T1/T2 relaxation times, and this effect, insofar as it depends on the presence of a signal-inducing metal, is lost more quickly upon dilution. For example, FIGS. 9-12 show the effect on T1 of several different MW weight fractions MW ca. 1,000 to 50,000 of an L-DOPA-melanin-gadolinium agent. FIG. 12A can be used to compare the effect of a different melanin precursor (3-amino-tyrosine) at the same molecular weight (ca. 50,000) as the L-DOPA agent (FIG. 12). The effectiveness of all these agents is compared to that of the highly toxic gadolinium chloride (FIGS. 9-12A) which shows approximately a 3.5 fold decrease in T1 (17.5 $(mmole/1)^{-1}sec^{-1}$). This compared favorably to the commercially available DTPA-Gd (4.5 $(mmole/1)^{-1}sec^{-1}$).

The melanin-Gd product can be prepared with or without the N-methyl-D-glucamine. The melanin agent with good aqueous solubility is easily derivatized or coupled to an antibody or other carrier using carbodiimide or alternative coupling technologies.

MRI provides a substantial range of tissue contrast without enhancement; however, increasing numbers of situations have demonstrated that contrast agents can provide the physician with improved diagnostic capabilities. The present invention provides a new class of clinically useful contrast agents that exhibit unusually strong influences on proton relaxation rates at concentrations substantially lower than metal chelates and polymeric agents currently available. Accordingly, the present inventive agent serves to decrease the effective agent concentration needed, has lowered toxicity and makes it more feasible to prepare tissue and/or organ specific agents by linking contrast agents to monoclonal antibodies or specific receptors.

The synthesis of a class of melanin polymers, which are stable free radicals containing various added paramagnetic metals is described herein. Control of the synthesis provides a range of agents with defined properties such as molecular weights that show different proton relaxation properties. For example, a high molecular weight (MW=50,000) gadolinium-melanin polymer shows a $T_1$ relaxivity of $2.45 \times 10^3$ $[mmole/1]^{-1}$ $sec^{-1}$ (n=3) compared to Gd-DTPA of 4.5 $[mmole/1]^{-1}$; $sec^{-1}$. This more than 500 fold effect is dependent upon molecular weight (MW) of the melanin polymer. For example, a gadolinium-melanin of intermediate MW (14,000 daltons) has a $T_1$ relaxivity of $9.5 \times 10^2$ $[mmole/1]^{-1} sec^{-1}$ whereas a low MW (8,000 daltons) agent is 26.6 $[mmole/1]^{-1} sec^{-1}$. The choice of monomeric melanin precursors and various metals for synthesis of the melanin agents yield materials that vary in proton relaxation effects. Superparamagnetic iron has also been incorporated into a melanin polymer and exhibits extremely fast relaxation rates (se FIG. 12B).

Image data is presented herein to show the efficacy of these new agents as both an oral contrast agent and a blood pool agent in a murine model. In addition a Gd-melanin polymer that exhibits a high $T_1$ relaxivity has been successfully coupled to a monoclonal antibody raised against the hormone, pancreatic polypeptide, and used has been demonstrated to retain its activity. In a rabbit model $^{111}$In incorporated into a melanin polymer has successfully imaged the pancreas; however, the antibody selectivity is low and a high background is observed.

Melanins are macromolecules consisting of mixtures of polymers that have a high degree of conjugation. This conjugation produces and/or stabilizes many of the properties that melanin possesses including its UV/Vis light absorption and its stable free radical properties. Melanin, as a stable free radical, causes a relaxation affect (acts as a contrast agent) by itself; however, incorporating a paramagnetic metal or complex into the melanin polymer enhances significantly its ability to affect contrast in MRI. Natural melanin may have some endogenous metals included but they do not cause a relaxation affect similar to the incorporated paramagnetic metal ions of the present inventive agent. The most likely biologic metals that could be present are iron and manganese and these metals included in a melanin polymer do enhance relaxivity but not as greatly as several other metals and gadolinium (see Tables 1-4). The high toxicity of gadolinium makes it unlikely to be available for incorporation into a natural melanin produced in vivo.

As has been known for a very long time, melanins may combine with metal ions. Preferred synthetic and natural melanins will bind metals such as gadolinium (or the other lanthanides) and produce an agent that substantially reduces the relaxation ($T_1$ and $T_2$) of a solution. However, upon dilution this affect is very rapidly lost due to dissociation of the metal ion from the preferred melanin.

The melanin-signal-inducing metal materials of the present invention do not release significant gadolinium (or other metals) upon dilution, upon extensive dialysis or even upon treatment with azides and amines; this added to a consequent effectiveness at low concentrations and great utility as image-enhancing agents.

Precursors for synthetic melanin include known published precursors such as catechol, L-dopa, dopamine, tyrosine, aminotyrosine, dihydroxytyrosines or phenylalanines, 1,8-dihydroxynaphthylene, for example. L-DOPA, dopamine, and aminotyrosine have primarily been used herein as melanin precursors but certainly do not limit the choice of melanin precursors. The polymerizations of the present invention were all conducted in an aqueous solvent; however, other solvents including alcohols, acetonitrile, tetrahydrofuran, e.g. may be used to tailor the desired contrast agent polymer as to structure, molecular weight, and final solubility.

Polymerization catalysts for such polymerizations of these or analogous materials include hydrogen peroxide, persulfates, peracids or peroxides, oxygen, sodium nitrite, i.e., essentially any strong oxidizing or free radical generating agent. In addition to these catalysts, azo-bisisobutyronitrile (a free radical polymerization agent) has been used and found to effectively produce a wide molecular range of polymers with improved solubilities. Other such free radical agents may also be used but have not yet been defined in detail.

Melanin may also be prepared by enzymatic procedures using a tyrosinase enzyme. While such enzymatic catalyses have not yet been performed in the presence of typical concentrations of paramagnetic metal ions used herein, it is anticipated that the requisite metals will inhibit tyrosinase activity and thus people and enzymatic catalysis. Metal ions, of course, must be present during melanin formation to result in secure incorporation; consequently, it is expected that a further research effort will be required to determine proper conditions allowing enzymatic synthesis of melanin-signal-inducing metal agents, and if it is practical to prepare them in this manner.

Solubilization of the melanin agents described herein may be outlined as follows. After molecular weight fractionation separates the melanins into various molecular weight ranges, it has been observed that some of the higher molecular weight materials tend to be insoluble in every solvent tested thus far (this is dependent upon polymerization conditions and precursors). A general procedure has been developed which produces a stable melanin or melanin-metal amine salt. For example an N-methylglucamine (meglumine) salt of the melanin will allow high molecular weight gadolinium-melanin to be easily brought into solution. This observation is completely general and significant. If one has an acidified melanin, an amine salt may be made that will allow production of a final product with solubility characteristics adapted to particular conditions such as full aqueous solubility or solubility in more lipid-like environments. For example, choosing a hydrophobic amine should produce a melanin that is soluble in non-polar materials. This technique has been used extensively for enhancing drug delivery.

A large number of metals have been employed in the syntheses of the present MRI agents and found to produce a melanin metal agent that affects the relaxation in a positive way for contrast alteration. Some are better than others but all are better than melanin alone. The list of utilized metals includes gadolinium; manganese; superparamagnetic iron; iron; praseodymium; ytterbium; dysprosium; and europium. That the particular metal is important is demonstrated by the fact that magnesium or zinc can be substituted and the resulting melanin-metal product does not show increased relaxation as compared to melanin without a metal. Magnesium is not paramagnetic and should not influence relaxation rates. In none of these melanin-metal combinations prepared according to the present inventive procedure, has the metal been removable by dialysis or treatment with azide followed by dialysis. The metal is an integral internal component of the melanin polymer.

Using other precursors such as, e.g., dopamine or aminotyrosine, for the melanin synthesis provides for ready synthetic manipulation of these agents. For example, such agents may be more readily coupled to antibodies, receptors or other substances than L-Dopa-based materials. This does not mean that they are necessarily better materials, only that they may be more versatile.

Control of melanin-metal molecular weight may be achieved by choice of polymerization catalyst and by reaction conditions and time of polymerization. While certain difference in relaxation rates of low molecular materials compared to high molecular weight materials has been found, the total amount of gadolinium or other paramagnetic metal is sometimes an important factor. However, the extent of incorporation of the metal into the conjugated polymer matrix is also important. The ability to obtain a series of molecular weight materials of different solubilities allows design of an agent specifically for a type of application. General blood pool agents should be of high molecular weight to prevent their entrance into certain capillary structures; lower molecular weight materials could be made permeable to the blood-brain barrier, for example.

Attachment of melanin-metal polymer to an antibody has been successful; however, the pilot antibody chosen did not facilitate imaging studies since it was not specific for a biological site. Nevertheless, these preliminary studies established the feasibility of the process—to produce a melanin-metal polymer coupled to an antibody and which has retained a strong relaxation effect as well as antibody activity.

Preliminary imaging experiments have shown that gadolinium-melanin is effective as both an oral contrast agent and a blood pool agent in an animal model. Experiments are currently underway to further define the ability of all the melanin-metal agents thus far prepared to act as in vivo contrast agents. Placement of these agents in specific organs and tissues to evaluate organ imaging effects (e.g. heart imaging; liver imaging, etc.) are forseen.

Several of the lanthanides have been used for many years as chemical shift agents in high resolution NMR spectroscopy (dysprosium, europium, etc.). The effect on imaging is not the only effect these agents may have; they may also affect chemical shift position in vivo. This has the potential to open a new area for in vivo diagnostic application. Melanin-metal combinations may be particularly useful as chemical shift agents.

Table 1 compares relaxivity of various prior and the present MRI agents.

TABLE 1

| AGENT | RELAXIVITY $[mmol/l]^{-1}sec^{-1}$ |
|---|---|
| Gadolinium - DTPA (Magnevist ®) | 4.5 |
| Gadolinium - DOTA | 3.8 |
| (in liver) | 6.7 |
| Manganese - DPDP | 2.8 |
| (in liver) | 21.7 |
| Gadolinium - Melanin MW = 50,000 | 2450.0 |

Table 1 illustrates the relative relaxivity induced by various gadolinium chelates as compared to gadolinium-melanin and illustrates the superiority of the latter.

Melanin was synthesized from L-dopa, 3-amino L-tyrosine, dopamine, and catechol incorporating various paramagnetic metal ions and varying temperature, catalyst, and reaction time in an attempt to determine the most effective metal ion-melanin polymer for use as a contrast agent in magnetic resonance imaging. It was found that L-dopa melanin-gadolinium synthesized with azobisisobutyronitrile (ABN) as catalyst produced a soluble, effective contrast agent with a prominent effect on $T_1$ relaxation times at concentrations less than 1 mg/ml. Gadolinium-labeled L-dopa melanin synthesized with ammonium persulfate as catalyst were more effective at lowering $T_1$ relaxation times, but that effect was greatly diminished in the effort to optimize solubility. Metals such as europium, praseodymium, and ytterbium also had an effect on relaxation time; however, that effect was not as notable as that produced by gadolinium. Superparamagnetic iron oxide had a dramatic effect on both $T_1$ and $T_2$ relaxation times; however, for use as a contrast agent a distinct ratio between $T_1$ and $T_2$ effect is necessary unless MRI equipment can take advantage of extremely short $T_2$ times (typical clinical imaging equipment cannot).

The following examples are presented to illustrate embodiments of the present invention and are not intended to limit the claimed scope of this invention unless specifically so stated in the appended claims.

EXAMPLE 1

Synthetic, Crystalization and Solubilization Protocols Utilized Herein

PROTOCOL A: Synthesis of Gd-labeled melanin from L-dopa

| Reagent: | Amount: | Molecular Weight: | Moles: |
| --- | --- | --- | --- |
| L-dopa | 1.25 g | 197 | .00635 |
| GdCl₃ | 0.25 g | 371 | .000625 |
| DMAP | 0.75 g | 122 | .00635 |
| ammonium persulfate | 0.15 g | 228 | .000625 |

Procedure

1. Dissolve DMAP (dimethylaminopyridine) in 100 ml distilled water
2. Add L-dopa (L-dihydroxyphenylalanine), add additional water if necessary to dissolve
3. Place in flask (2×volume minimum)
4. Add GdCl₃ and dissolve
5. Add ammonium persulfate (catalyst)

PROTOCOL B: Synthesis of melanin from 3-amino L-tyrosine

| Reagents: | Amount: | Molecular Weight: | Moles: |
| --- | --- | --- | --- |
| 3-amino L-tyrosine | 1,81 g | 289 | 0.00625 |
| DMAP | 0.75 g | 122 | 0.00635 |
| GdCl₃ | 0.25 g | 371 | 0.000625 |
| ammonium persulfate | 0.15 g | 228 | 0.000625 |

Procedure

As Protocol A except substitute 1.81 g 3-amino L-tyrosine for L-dopa.

PROTOCOL C: Recrystallization of catechol

Dissolve catechol into heated toluene and allow to cool, recrystallizing catechol. Filter catechol from toluene solution.

PROTOCOL D: Synthesis of melanin from 3-amino L-tyrosine

| Reagents: | Amount: | MW: | Moles: |
| --- | --- | --- | --- |
| 3-amino L-tyrosine | 1.81 g | 289 | .00625 |
| DMAP | 0.75 g | 122 | .00635 |
| GdCl₃ | 0.25 g | 371 | .000625 |
| ammonium persulfate | 0.15 g | 228 | .000625 (10%) |

Procedure

Same as for Protocol A

PROTOCOL E: Solubilization of melanin

| Reagent: | Amount: |
| --- | --- |
| Synthesized melanin | 100–150 ml |
| N-methyl D-glucamine | 5 g |

Procedure

1. Add 5 g NMEG (N-methyl D-glucamine) to melanin
2. Heat in round-bottom flask at 50° C. overnight

EXAMPLE 2

Synthesis 1, 2, 3, 4

Melanin was synthesized from catechol in an attempt to optimize conditions for highest yield. Catechol was first purified by recrystallization (See Protocol C). Benzoyl peroxide (7 g) to be used as a catalyst was added to 175 ml stirred acetonitrile preheated to 55° C. Recrystallized catechol (5g) was added to the above solution. Triethylamine 2 ml in 25 ml acetonitrile was then added. The solution was allowed to react overnight. Following the reaction, the solution (now a dark brown color) was rotoevaporated to remove the acetonitrile. The remaining product was precipitated with ether and, the supernatant decanted, and the residue allowed to dry. The precipitant was dissolved in methanol and re-precipitated with ether: the ether was again decanted and the precipitant was dried (by vacuum) and saved. The ether insoluble material of both precipitations was dissolved in methanol and saved. This procedure yielded 0.51 g precipitate. Synthesis 2 was a repeat of this procedure and yielded 0.441 g precipitate. Synthesis 3 was modified by using 20 ml triethylamine rather than 2 ml. As a result of this modification, the sample was difficult to precipitate. Since the triethylamine was not all removed with the acetonitrile in rotoevaporation, the excess amine remained in the sample. It was necessary to wash the non-ether soluble material (dissolved in methanol) prior to precipitation with 0.12 M HCl solution, which fully precipitated the melanin while leaving the triethylamine in solution. The mixture was then filtered and the filtrate was washed repeatedly with water. The filtrate was then allowed to dry. Synthesis 4 was a repeat of synthesis 3 except the reaction was run at room temperature. The non-ether soluble precipitate was dissolved in chloroform rather than methanol prior to being washed with HCl and water. This procedure yielded 1.033 g.

EXAMPLE 3

Synthesis 5

Melanin was synthesized from dopamine with ammonium persulfate as catalyst. Dopamine (1 g) was dissolved in 100 ml water. Ammonium persulfate (0.1184 g) was added to the dopamine solution. The solution was allowed to react overnight. The resultant melanin was insoluble in water as well as methanol and dimethylformamide. Due to this insolubility nothing further has yet been accomplished with this product.

EXAMPLE 4

Synthesis 6

Melanin was synthesized from dopamine with ammonium persulfate as catalyst. The primary difference between this and the previous reaction is the addition of 0.5 ml benzoyl chloride in 4.5 ml methylene chloride to the reacting solution. The resultant sample was still insoluble in water and several organic solvents.

EXAMPLE 5

Synthesis 8

Melanin was synthesized from L-dopa in an attempt to incorporate gadolinium ions (Gd+++) for use in contrast agent studies. Dimethylaminopyridine (DMAP) (3 g) was dissolved in 300 ml water. L-dopa (5 g) was added to the solution and stirred until completely dissolved. The L-dopa was somewhat difficult to dissolve. $GdCl_3$ (1 g) was added to the solution. The $GdCl_3$ did not completely dissolve and turned the solution a cloudy green color upon its addition. Ammonium persulfate (0.6) (catalyst) was added to the solution. A reaction occurred almost immediately after the catalyst was added and was allowed to run for 2 weeks. The reacted solution was then dialyzed against water (4L) with 6-8K molecular weight cutoff (mwco) Spectrapor dialysis tubing for 1 day to remove excess catalyst, DMAP, and unreacted reagents. The dry weight of 10 ml of the solution indicated a concentration of 7.7 mg/ml. T1 relaxation time of a 1:100 dilution of the sample was 188 msec, although the solution was not 100% soluble and the solid matter might have introduced error into the results.

EXAMPLE 6

Synthesis 10

Figure 7A:
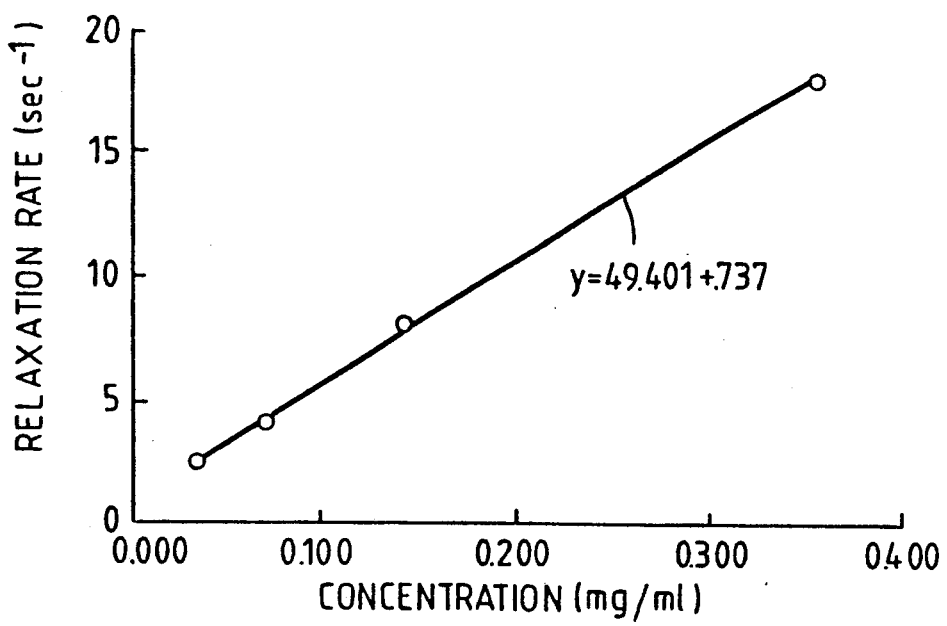
FIG. 7 illustrates the effect of a particular preparation (FIG. 7A: synthesis 10.
FIG. 7B: synthesis 12.
FIG. 7C: synthesis 14) of a melanin gadolinium combination upon $T_1$ relaxation times.
Figure 9:
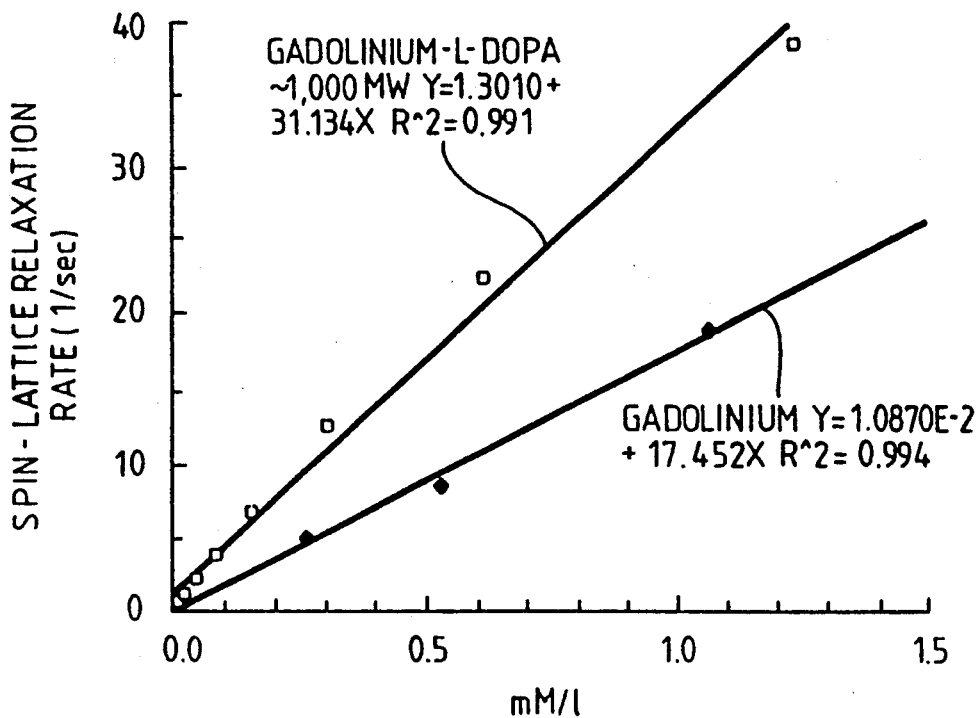
Figure 10:
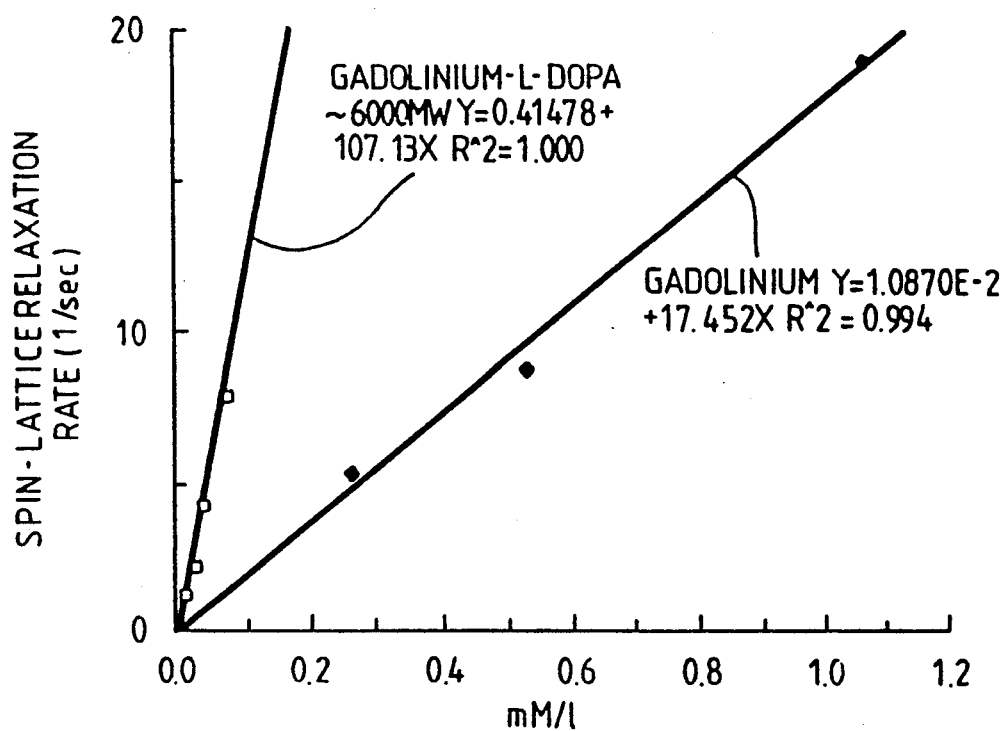

Melanin was synthesized from L-dopa while incorporating gadolinium ions under varying reaction conditions. The basic procedure noted in Synthesis 8 was used, with reagents in quantities as noted above. The reaction was allowed to run 1 day. The solution was first dialyzed against water (4L) with 6-8K mwco dialysis tubing. This fraction was then dialyzed against water with a 50,000 MWCO dialysis tubing. This and other Gd-melanin solutions, even if soluble immediately following reaction, tended to become more insoluble with time. While Synthesis 8 material was already partially insoluble immediately after the reaction, the material from the present synthesis was at first soluble, probably due to decreased reaction time. Dry 10 weight of a 10 ml solution sample indicated a concentration of 3.55 mg/ml. The 50,000 MW sample was particularly effective at high concentrations for T1 relaxation time (see FIG. 7A). Relaxivity of this sample is 2,470 $[mmole/1]^{-1}sec^{-1}$

EXAMPLE 7

Synthesis 11

Melanin was synthesized from L-dopa as a control for Synthesis 10. The conditions were identical to those in Synthesis 10, but this solution contained no gadolinium. Melanin without gadolinium incorporated tended to be more soluble than that with metal ions. It also tended to be lighter in color than Gd-melanin. Dry weight of a 10 ml sample indicated a concentration of 1.75 mg/ml. Relaxation measurements of melanin without gadolinium have much less effect on T1 relaxation times. The relaxivity of the melanin control without gadolinium is 4.95 $[mmole/1]^{-1}sec^{-1}$ This relaxivity compares favorably to gadolinium chloride (17.5 $[mmole/1]^{-1}sec^{-1}$) and to Gd-gadolinium-DTPA (Magnevist®)) (4.5 $(mmole/1)^{-1}sec^{-1}$.

EXAMPLE 8

Synthesis 12

Melanin was synthesized from L-dopa incorporating gadolinium ions under different conditions. The procedure follows that in Protocol A but with the following reagent quantities: DMAP (1.5 g), L-dopa (2.5 g), $GdCl_3$ (0.5 g), and ammonium persulfate (0.3 g). The solution was heated in a round-bottom flask with an oil bath set at 50° C. overnight. The solution was first dialyzed against water (4L) with 6-8K mwco dialysis tubing and then sequentially with 50,000 MWCO tubing. Dry weight of a 10 ml sample indicated a concentration of 1.2 mg/ml. This sample also had a significant effect on T1 relaxation times, although not as prominent as that in Synthesis 10 (see FIG. 7B). Decreased run time might have accounted for this discrepancy; however, it is also possible that, given the amorphous nature of the melanin polymer, the reaction is not precisely repeatable. Relaxivity of this sample was estimated at least 1,918 $(mmole/1)^{-1}sec^{-1}$ since the exact molecular weight was not known.

EXAMPLE 9

Synthesis 13

Melanin was synthesized from L-dopa as a control for Synthesis 12. Procedure was identical to that of Synthesis 12, except that the sample contained no $GdCl_3$. Dry weight of a 10 ml sample indicated a concentration of 1.2 mg/ml. T1 relaxation times indicate some small effect at high concentrations; however, it is noted that the effect seems to level off at about 2400-2500 msec. Since this is the approximate relaxation time of water, it is presumed that in all extremely dilute samples, the relaxation time would appear at about the same point. The equation of the line present in most rate graphs indicates an essentially constant y-intercept of 0.4 reciprocal seconds, or about the relaxation rate of water, as is expected (relaxation rate=0.47 concentration $(\mu g/1)+0.42$). The molecular weight of this sample is approximately four times the molecular weight of control synthesis 11; consequently, the relaxivity is ca. 5.8 $(mmole/1)^{-1}sec^{-1}$.

EXAMPLE 10

Synthesis 14

Melanin was synthesized from L-dopa incorporating gadolinium ions under varying conditions. The procedure follows that in Protocol A with the following reagent quantities: DMAP (2.9 g), L-dopa (4.95 g), $GdCl_3$ (1 g), and ammonium persulfate (0.6 g). The reaction was allowed to run 4 weeks. The sample was dialyzed against water (4 L) with 6-8K mwco dialysis tubing. The sample had almost completely precipitated out by the end of dialysis. Dry weight of 10 ml of the sample indicated a concentration of 9.3 mg/ml. The slope of the T1 relaxation rate vs. concentration line is almost identical to that in Synthesis 10 (see FIG. 7C); presumably, the sample (if allowed to react long enough) reaches a saturation point beyond which the only effect is to alter yield and solubility.

EXAMPLE 11

Synthesis 15

Melanin was synthesized from L-dopa as a control to Synthesis 14. Procedure was identical to that in Synthesis 14, including the reagent quantities except that the sample contained no GdCl$_3$. The resultant material was also almost completely insoluble in water. Dry weight of 10 ml of the sample indicated a concentration of 8.1 mg/ml. The effect on T1 relaxation time is almost negligible. It is possible that this diminished effect over other samples of melanin without metal ions was due to the nature of the synthesis. Two ways to synthesize melanin are by oxidation or by free-radical induced polymerization. The free-radical element of the melanin is that part which itself may affect relaxation time. Ammonium persulfate is both a free-radical polymerizer and an oxidant. It is thought that free-radical polymerization occurs faster than oxidation, so the initial segment of the reaction is probably primarily by that process. However, the melanin polymer is highly malleable; it alters from a state containing free-radicals to a completely oxidized state rather easily. If the reaction is left running past a certain point, the oxidizing nature of the catalyst may alter the majority of the free-radicals to a more stable state, thus eliminating the free-radical component of the polymer and, coincidentally, the polymer's effect on relaxation time. (See also Syntheses 28, 29.)

EXAMPLE 12

Synthesis 16

Melanin was synthesized from L-dopa incorporating gadolinium ions under different conditions. Procedure followed Protocol A with the following reagent quantities: DMAP (1.5 g), L-dopa (2.5 g), GdCl$_3$ (0.5 g), and ammonium persulfate (0.3 g). The solution was placed in a round-bottom flask in an oil bath and heated to reflux (100° C.). The reaction was allowed to run 1 day. The solution was dialyzed against water (4 L) with 6–8K mwco dialysis tubing. Dry weight of 10 ml of the sample indicated a concentration of 2.5 mg/ml. T1 relaxation time of a 1:10 dilution of the sample was 389 msec.

EXAMPLE 13

Synthesis 17

Melanin was synthesized from L-dopa as a control to Synthesis 16. The procedure followed was that of Syntheses 16 exactly except that the sample contained no GdCl$_3$. Dry weight of 10 ml of the sample indicated a concentration of 1 mg/ml.

EXAMPLE 14

Synthesis 18

Melanin was synthesized from L-dopa incorporating gadolinium ions under the following conditions. The procedure followed Protocol A with reagents as follows: DMAP (1.5 g), L-dopa (2.5 g), GdCl$_3$ (0.5 g), and ammonium persulfate (0.6 g) (20% catalyst rather than the previous 10%). The mixture was allowed to react 1 day. The solution was dialyzed against water (4L) with 6–8K mwco dialysis tubing. Dry weight of 10 ml of the sample indicated a concentration of 0.8 mg/ml. The extra ammonium persulfate might inhibit the reaction, causing the decreased yield thus shown. However, it is doubtful that the nature of the reaction was such that it would have caused the greater than tenfold decrease in effect on the relaxivity (35.2 (mmole/l)$^{-1}$sec$^{-1}$). The Gd-labeled melanin polymer had a diphasic effect, with a decreased slope at very low concentrations.

EXAMPLE 15

Synthesis 19

Melanin was synthesized from L-dopa as a control for Synthesis 18. Procedure was identical to that in Synthesis 18 except that the sample contained no GdCl$_3$ Dry weight of 10 ml of the sample indicated a concentration of 1.4 mg/ml. The relaxation rate of this sample showed a characteristic effect on relaxation measurements; that is to say, little to none. The relaxation measurements were in a scattered pattern, probably as a result of the difficulties encountered in measuring long relaxation times. The relaxivity of the control was 1.6 (mmole/l)$^{-1}$sec$^{-1}$.

EXAMPLE 16

Synthesis 20

Melanin was synthesized from L-dopa incorporating gadolinium ions under the following conditions. The procedure followed Protocol A with reagents as follows: DMAP (0.75 g), L-dopa (1.25 g), GdCl$_3$ (0.25 g), and ammonium persulfate (0.15 g). The reaction was run at room temperature for 30 minutes. The solution was dialyzed against water (4L) with 3500 mwco dialysis tubing, and then dialyzed against water (1L) with 12–14K mwco dialysis tubing, saving both divisions of substance. Dry weight of 10 ml of the two samples indicated a concentration of 2.1 mg/ml for the 12–14K MW dialyzed material and a negligible amount of difference in weights between the 3500 dialyzed and 12–14K MW dialyzed material. The 14,000 MW material had a relaxivity of 211 (mmole/l)$^{-1}$sec$^{-1}$.

EXAMPLE 17

Synthesis 21

Melanin was synthesized from L-dopa as a control for Synthesis 20. Procedure followed that of Synthesis 20 exactly except for the absence of GdCl$_3$. Dry weight of 10 ml of the two samples indicated a concentration of 0.7 mg/ml for 12–14K MW dialyzed material and a negligible amount of material between 3500 and 12–14K MW. The 14,000 MW material had a relaxivity of 8.6 (mmole/l)$^{-1}$sec$^{-1}$.

EXAMPLE 18

Synthesis 22

Melanin was synthesized from 3-amino L-tyrosine incorporating gadolinium ions. Procedure followed Protocol D. The solution was allowed to react 4 days at room temperature. The substance was then dialyzed against water (4L) with 6–8K mwco dialysis tubing. This reaction ran neither quickly nor effectively. Dry weight of 10 ml of the sample indicated a concentration of 0.4 mg/ml. T1 relaxation time of a 1:10 dilution of the sample was 1266 msec and the relaxivity of the material with a MW of 8,000 was 30.7 (mmole/l)$^{-1}$sec$^{-1}$. (See FIG. 12A)

EXAMPLE 19

Synthesis 23

Melanin was synthesized from 3-amino L-tyrosine as a control for Synthesis 22. Procedure followed that of Synthesis 22 exactly except that the sample contained no GdCl$_3$. Dry weight of 10 ml of the sample indicated a concentration of 0.2 mg/ml and the relaxivity was 10.9 (mmole/l)$^{-1}$sed$^{-1}$.

EXAMPLE 20

Synthesis 24

Melanin was synthesized from 3-amino L-tyrosine incorporating gadolinium ions as described in synthesis 22. In an effort to improve yield and thus relaxation data, the amount of catalyst was increased to 0.75 g ammonium persulfate (50% catalyst). The solution was allowed to react 1 day at room temperature. The solution was then dialyzed against water (4L) with 6–8K mwco dialysis tubing. The increased catalyst resulted in more insoluble material; however, dry weight of 10 ml of the sample indicated a concentration of 2.2 mg/ml, a much higher yield than that obtained in Synthesis 22.

EXAMPLE 21

Synthesis 25

Melanin was synthesized from 3-amino L-tyrosine as a control for Synthesis 24. Procedure followed that for Synthesis 24 exactly except for the absence of GdCl$_3$. Dry weight of 10 ml of the sample indicated a concentration of 3.1 mg/ml and the relaxivity was 39.8 (mmole/l)$^{-1}$sec$^{-1}$.

EXAMPLE 22

Synthesis 26

Melanin was synthesized from L-dopa incorporating gadolinium ions and N-methyl D-glucamine was then used to ensure complete solubility. Procedure followed Protocol A. The solution was allowed to react 210 minutes. The solution was then placed in a round-bottom flask in an oil bath at 50° C. 5 g N-methyl D-glucamine (NMEG) was added and the solution was heated overnight. The solution was then dialyzed against water (4L) with 6–8K mwco dialysis tubing. The dialysate was rotoevaporated and redialyzed with 3500 mwco dialysis tubing. The solution may continue to react while being solubilized; to prevent this, it may be necessary to dialyze the solution prior to solubilization with NMEG. Dry weight of 10 ml of the sample indicated a concentration of 4.42 mg/ml of a 14,000 MW sample that had a relaxivity of 20.6 (mmole/l)$^{-1}$sec$^{-1}$.

EXAMPLE 23

Synthesis 27

Melanin was synthesized from L-dopa as a control for Synthesis 26. Procedure followed that of Synthesis 26 exactly except that the sample contained no GdCl$_3$. Dry weight of 10 ml of the sample indicated a concentration of 7.21 mg/ml and the 14,000 MW sample had a relaxivity of 0.46 (mmole/l)$^{-1}$sec$^{-1}$.

EXAMPLE 24

Cleaving of Samples from Syntheses 26, 27 with hydrogen peroxide was done as follows. A sample from both Synthesis 26 and Synthesis 27 was cleaved with 10% hydrogen peroxide in an attempt to obtain low molecular weight material. A 10 ml sample of #26 was placed in a round-bottom flask. Equipped with a condenser and magnetic stir bar, 10 ml 10% hydrogen peroxide was added dropwise. The solution was allowed to react for 6 days and was then dialyzed against water (1L) with 12–14K mwco dialysis tubing. The process was repeated with a 10 ml sample from #27. Either the solution was unduly diluted or metal ions were lost, as relaxation measurements before and after dialysis indicated considerable loss of effect. The substance also appeared bleached; it was, e.g., more yellow in color than uncleaved melanin.

EXAMPLE 24

Synthesis 28

Melanin was synthesized from L-dopa while incorporating gadolinium ions and using sodium nitrite as catalyst. The procedure followed both Protocol A and Protocol E (solubilization). However, 43 mg sodium nitrite (10%) was substituted for ammonium persulfate. The soluble mixture was allowed to react for 30 minutes and was then dialyzed against water (4L) with 3500 mwco dialysis tubing. It was next dialyzed against water (1L) with 12–14K mwco dialysis tubing but the dialysate was not saved since only a negligible amount of material dialyzed out. Dry weight of 10 ml of the dialyzed sample indicated a concentration of 3.4 mg/ml. The sample had a MW of 14,000 and exhibited a relaxivity of 149.8 (mmole/l)$^{-1}$sec$^{-1}$.

EXAMPLE 25

Synthesis 31

This reaction was incidentally noted. DMAP (0.75) was dissolved in 100 ml water. L-dopa (1.25g) was then added to the DMAP solution. The resulting solution was covered and left overnight. The L-dopa reacted to form a melanin without catalysis other than that by oxygen dissolved in the water and from the surrounding air. The solution was then dialyzed against water (4L) with 6–8K mwco dialysis tubing. Relaxivity of the 8,000 MW material was 28.0 (mmole/l)$^{-1}$sec$^{-1}$.

EXAMPLE 26

Synthesis 32

Melanin was synthesized from L-dopa while incorporating gadolinium ions in an attempt to obtain low-molecular weight, soluble material without use of NMEG. The procedure followed protocol A, except 0.015 g ammonium persulfate (1%) was used instead of the usual 10% catalyst. The solution was allowed to react 10 minutes at room temperature and was then dialyzed against water (4L) with 3500 mwco dialysis tubing for 4 days. It was next dialyzed against water (1L) with 12–14K mwco dialysis tubing; however, a negligible amount of material dialyzed out, possibly because any substance that was under 12K MW was insoluble. The solution was solubilized overnight with 5 ml triethylamine at 60° C. The solution was then redialyzed against water (4L) with 6–8K mwco dialysis tubing. The relaxivity of the 8,000 MW material was 54.5 (mmole/l)$^{-1}$sec$^{-1}$.

EXAMPLE 27

Synthesis 33

Melanin was synthesized from L-dopa as a control for Synthesis 32. Procedure followed that for Synthesis 32 exactly but contained no GdCl$_3$. Relaxivity was 2.92 (mmole/l)$^{-1}$sec$^{-1}$.

EXAMPLE 28

Synthesis 34

Melanin was synthesized from L-dopa incorporating gadolinium ions in an attempt to obtain low-molecular weight Gd-melanin. The procedure followed Protocol A. 0.015 g ammonium persulfate (1% catalyst) was substituted for the standard amount. The reaction was allowed to run 10 minutes. After 10 minutes, 1% potassium iodide was added to the solution to halt the reaction. The solution was then dialyzed against water (4L) with 1000 mwco dialysis tubing and 6–8,000 MWCO tubing and the fraction <6,000 was evaluated. The relaxivity of the sample was 22.2 (mmole/1)$^{-1}$sec$^{-1}$.

EXAMPLE 29 tocol A but 2 ml of 50 mg/ml superparamagnetic iron oxide was substituted for $GdCl_3$. The solution was allowed to react 3 days. The solution was then solubilized with 10 g NMEG. The solution was dialyzed initially against 4L water with 3500 mwco tubing. A T1 relaxation time of 16.6 (mg/ml)$^{-1}$sec$^{-1}$ and a T2 of 76.3 (mg/ml)$^{-1}$sec$^{-1}$ was measured for the superparamagnetic iron-melanin agent fraction that had a MW ca. 50,000. (See FIG. 12B).

TABLE 2

Summary of Certain Syntheses and Yields

| Synthesis[1] | Run Time | metal | precursor | catalyst[2] | soluble[3] | Yield |
|---|---|---|---|---|---|---|
| 8 | 2 wks. | $Gd^{+++}$ | L-dopa | 1 | none | 7.7 mg/ml |
| 10 | 1 day | $Gd^{+++}$ | L-dopa | 1 | none | 3.55 mg/ml |
| 11 | 1 day | none | L-dopa | 1 | none | 1.75 mg/ml |
| 12 | 1 day | $GD^{+++}$ | L-dopa | 1 | none | 1.2 mg/ml |
| 13 | 1 day | none | L-dopa | 1 | none | 1.2 mg/ml |
| 14 | 4 wks | $Gd^{+++}$ | L-dopa | 1 | none | 9.3 mg/ml |
| 15 | 4 wks | none | L-dopa | 1 | none | 8.1 mg/ml |
| 16 | 1 day | $Gd^{+++}$ | L-dopa | 1 | none | 2.5 mg/ml |
| 17 | 1 day | none | L-dopa | 1 | none | 1.0 mg/ml |
| 18 | 1 day | $Gd^{+++}$ | L-dopa | 2 | none | 0.8 mg/ml |
| 19 | 1 day | none | L-dopa | 2 | none | 1.4 mg/ml |
| 20 | 30 min. | $Gd^{+++}$ | L-dopa | 1 | none | 2.1 mg/ml |
| 21 | 30 min. | none | L-dopa | 1 | none | 0.7 mg/ml |
| 22 | 4 days | $Gd^{+++}$ | 3-$NH_2$L-Tyr[4] | 1 | none | 0.4 mg/ml |
| 23 | 4 days | none | 3-$NH_2$L-Tyr[4] | 1 | none | 0.2 mg/ml |
| 24 | 1 day | $Gd^{+++}$ | 3-$NH_2$L-Tyr[4] | 3 | none | 2.2 mg/ml |
| 25 | 1 day | none | 3-$NH_2$L-Tyr[4] | 3 | none | 3.1 mg/ml |
| 26 | 30 min. | $Gd^{+++}$ | L-dopa | 1 | 1 | 4.42 mg/ml |
| 27 | 30 min. | none | L-dopa | 1 | 1 | 7.21 mg/ml |
| 28 | 30 min. | $Gd^{+++}$ | L-dopa | 4 | 1 | 3.4 mg/ml |
| 32 | 10 min. | $Gd^{+++}$ | L-dopa | 5 | 2 | 1.30 mg/ml |
| 33 | 10 min. | none | L-dopa | 5 | 2 | 1.23 mg/ml |
| 34 | 10 min. | $Gd^{+++}$ | L-dopa | 5 | none | 3.24 mg/ml |
| 35 | 10 min. | none | L-dopa | 5 | none | 1.18 mg/ml |
| 36 | 2 days | $Gd^{+++}$ | 3-$NH_2$l-Tyr[4] | 4 | none | 1.47 mg/ml |
| 37 | 2 days | none | 3-$NH_2$L-Tyr[4] | 4 | none | 0.36 mg/ml |
| 38 | 2 days | $Gd^{+++}$ | dopamine | 4 | 1* | 2.64 mg/ml |
| 39 | 2 days | none | dopamine | 4 | 1* | 0.47 mg/ml |
| 40 | 2 days | $Gd^{+++}$ | 3-$NH_2$L-Tyr[4] | 4 | none | 1.38 mg/ml |
| 42 | 2 days | $Gd^{+++}$ | L-dopa | 6 | none | 6.47 mg/ml |
| 43 | 2 days | none | L-dopa | 6 | none | 5.08 mg/ml |
| 44 | 2 days | $Gd^{+++}$ | L-dopa | 6 | none | 6.80 mg/ml |
| 45 | 2 days | none | L-dopa | 6 | none | 2.75 mg/ml |
| 50 | 3 days | FeO | L-dopa | 1 | 1 | 9.05 mg/ml |
| 51 | 30 min. | $Fe^{+++}$ | L-dopa | 1 | 1 | 2.80 mg/ml |
| 52 | 30 min. | $Fe^{++}$ | L-dopa | 1 | 1 | 1.00 mg/ml |
| 54 | 3 days | $Gd^{+++}$ | L-dopa | 7 | none | 2.21 mg/ml |
| 55 | 3 days | none | L-dopa | 7 | none | 0.55 mg/ml |
| 56 | 30 min. | $Pr^{+++}$ | L-dopa | 1 | 1 | 2.63 mg/ml |
| 57 | 30 min. | $Eu^{+++}$ | L-dopa | 1 | 1 | 3.64 mg/ml |
| 58 | 30 min. | $Yb^{+++}$ | L-dopa | 1 | 1 | 2.92 mg/ml |

| [2]number | catalyst |
|---|---|
| 1 | 10% ammonium persulfate |
| 2 | 20% ammonium persulfate |
| 3 | 10% sodium nitrite |
| 4 | 1% ammonium persulfate |
| 5 | 10% azobisisobutyronitrile (ABN) |
| 6 | 100% benzoyl peroxide |
| 7 | 10% t-butyl hydroperoxide |
| [3]number | method of solubilization |
| 1 | 5 g N-methyl D-glucamine overnight @ 50° C. |
| 2 | 5 ml triethylamine overnight |

[4]3 amino L-tyrosine

Synthesis 35

Melanin was synthesized from L-dopa as a control for Synthesis 34. Procedure followed that for synthesis 34 exactly but the sample contained no $GdCl_3$ and the relaxivity was 1.8 (mmole/1)$^{-1}$sec$^{-1}$.

EXAMPLE 30

Synthesis 50

Melanin was synthesized from L-dopa incorporating superparamagnetic iron oxide. Procedure followed Pro-

EXAMPLE 31

Generalized Procedure for Melanins from L-DOPA Using Persulfate

A primary solution was prepared as follows: 1.25 gr (0.006 moles) L-DOPA and 0.75 gr (0.006 moles) of dimethylaminopyridine (DMAP) were dissolved in water (300 ml) with stirring. Ammonium persulfate, 0.15 g (0.007 moles) was added as a solid and the solution stirred for another 30 minutes.

When $Zn^{2+}$/L-DOPA-melanin was being prepared 1.80 g $ZnSO_4$ was added to the primary solution. When $Mn^{2+}$/L-DOPA-melanin was being prepared 0.124 g $MnCl_2$ was added to the primary solution. When $Cu^{2+}$/L-DOPA-melanin was being prepared 0.156 g $CuSO_4$ was added to the primary solution. Other lanthanides including praseodymium, europium, ytterbium and dysprosium may be likewise incorporated in melanin.

Solubilization Procedure

All melanin-metal compounds do not require solubilization. Differences in precursor, catalyst, or molecular weight can cause insolubility. The following procedure was used to solubilize otherwise insoluble L-DOPA melanins.

5 gr N-methylglucamine (x moles) or other amine added to acidified and washed metal/L-DOPA-melanin solutions and heated at 50° C. overnight (12–18 hrs). Other melanins, if solubilization is necessary, will be solubilized through salt formation or other well-known procedures.

Dialysis procedure

L-DOPA-melanin or metal /L-DOPA-melanin solutions, with or without solubilizing agent were dialyzed using a series of molecular weight cutoff membranes to first remove unreacted starting materials and low molecular weight contaminants, and then to fractionate the material into several broad molecular weight ranges. The molecular weight cutoff dialysis membranes (Spectra/POR3 ®) were 1,000; 3,500; 8,000; 14,000; and 50,000 giving molecular weight ranges for the melanin of 1,000–3,000; 3,500–8,000; 8,000–14,000; 14,000–50,000; and >50,000.

FIGS. 9–12 show the effect of different molecular weights on the relaxivity of gadolinium-L-DOPA-melanin samples. The relaxivity for gadolinium chloride is also plotted on the same Figures for comparison.

Experimental protocol relating to data of Table 3 (and also elsewhere herein) were as follows. Melanin and melanin-gadolinium polymers were sized according to molecular weight and the amount of gadolinium was measured by atomic absorption and x-ray fluorescence techniques. Serial dilutions were prepared with characterized and weighed samples that were dissolved in water and solubilized as required, producing solutions of known concentrations of melanin or melanin-metal polymers. Spin-lattice (T1) and spin-spin (T2) relaxation measurements were done at 0.25T (10MHz) on sample volumes of about 10 ml using a pulsed FT Praxis II. Preliminary T1, and T2 measurements have also been performed at 2T and 7T.

TABLE 3

| MONOMER | METAL | MW | RELAXIVITY 1/(mM/L) sec | Gd mM/L |
|---|---|---|---|---|
| L-DOPA | | ca. 1000 | 0.04 | |
| L-DOPA | Gd | ca. 1000 | 31.1 | 1.83 |
| L-DOPA | | ca. 6000 | 0.27 | |
| L-DOPA | Gd | ca. 6000 | 107 | 1.02 |
| L-DOPA | | 50,000 | 3.55 | 0.30 |
| L-DOPA | Gd | 50,000 | 148 | |
| L-DOPA | | 50,000 | 4.95 | |
| L-DOPA | Gd | 50,000 | 221 | 2.37 |
| 3-NH$_2$-LTyr | | 50,000 | 5.91 | |
| 3-NH$_2$-LTyr | Gd | 50,000 | 30.0 | 2.72 |
| Dopamine | | 50,000 | 0.57 | |

TABLE 3-continued

| MONOMER | METAL | MW | RELAXIVITY 1/(mM/L) sec | Gd mM/L |
|---|---|---|---|---|
| Dopamine | Gd | 50,000 | 0.785 | <0.27 |
| Dopamine | | 50,000 | 0.51 | |
| Dopamine | Gd | 50,000 | 0.82 | <0.27 |
| Gd | Gd | 157.25 | 19.2 | 2.69 |

Table 4 represents a comparative study of the relaxivity of a variety of agents that shows the efficacy of the melanin-metal contrast agents.

TABLE 4

| AGENT | RELAXIVITY 1/(mM/L) (sec) |
|---|---|
| 3-NH$_2$-LTyr-Melanin | 1.4 |
| Manganese-DPDP | 2.8 |
| Dopamine-Melanin | 3.6 |
| Gadolinium-DOTA | 3.8 |
| Gadolinium-DTPA (Magnevist ®) | 4.5 |
| L-DOPA-Melanin | 4.8 + 2.5 (n = 8) |
| Gadolinium-DOTA (in liver) | 6.7 |
| Gadolinium Chloride | 17.5 |
| L-DOPA-MELANINS | |
| Ferric Iron | 14.3 |
| Praseodymium | 18.6 |
| Europium | 19.8 |
| Ferrous iron | 22.3 |
| Ytterbium | 331.0 |
| Superparamagnetic iron | 830.0 |
| Gadolinium | 2470.0 |
| 3-NH$_2$-LTyr-Melanin-Gd | 39.8 |
| Dopamine-Melanin-Gd | 325.0 |

EXAMPLE 32

Coupling of Gd-melanin to antibody

General Procedures

The following is a brief outline of work to date concerning the coupling of Gd-melanin to antibodies. The main reactions (synthesis of melanin and coupling of melanin to protein) and deductive support work provide a major portion of the following section.

The general Coupling Reaction involves the following reagents and procedures:

| Reagents: | |
|---|---|
| Melanin or Gd-Melanin | 10 ml |
| 0.33M EDC (1-(3-dimethylaminopropyl)-3-ethylcarbodiimide | 40 µl |
| 0.89M DMAP (4-dimethylaminopyridine) | 36 µl |
| Protein (control protein or antibody) | 25 mg |

Procedure

Prepare sand or water bath by warming to 35° C.
Mix melanin, EDC, and DMAP in reaction flask.
Stir at 35° C. for 30 minutes.
Remove from bath and cool to room temperature (26° C.).
Add protein (including IgG) to reaction flask.
Stir at room temperature overnight.

Variations in scale of this procedure were performed utilizing a wt:wt ratio. This was necessary due to the inability to determine molar ratios for IgG solutions. Clone BSA-33 contains 30.5 mg/ml total protein, of which 3.7 mg/ml is IgG$_{2a}$. The other proteins of this material are serum albumins and interstitial fluid proteins of indeterminate size.

General Melanin Synthesis Reaction

| Reagents: | | |
|---|---|---|
| Precursor | 0.00634 moles | |
| DMAP | 0.00614 moles | 122.17 MW |
| ABN (azobisisobutyronitrile) | 0.00061 moles | 164.21 MW |
| $H_2O$ | 6.94444 moles | 18.02 MW |

Procedure

Prepare oil bath for reaction by warming to 70° C.
Add 125 ml of water to a 250 erlenmeyer flask.
Add 0.75 g DMAP to flask and stir until completely in solution
Add melanin precursor to flask and stir until completely in solution.
Add 0.1 g of ABN (azobisisobutyronitrile) to flask and stir at 70° C. until completion (solution will get progressively darker with time; stir until no change is apparent).

General Gd-Melanin Synthesis Reaction

| Reagents: | | |
|---|---|---|
| Precursor | 0.00634 moles | |
| DMAP | 0.00614 moles | 122.17 MW |
| ABN | 0.00061 moles | 164.21 MW |
| $GdCl_3$ Hexahydrate | 0.00067 moles | 370.70 MW |
| $H_2O$ | 6.94444 moles | 18.02 MW |

Procedure

Prepare oil bath for reaction by warming to 70° C.
Add 125 ml of water to a 250 erlenmeyer flask.
Add 0.75 g DMAP to flask and stir until completely in solution.
Add precursor to flask and stir until completely in solution.
Add 0.25 g GdCl to flask and stir until completely in solution.
Add 0.1 g of ABN to flask and stir at 70° C. until completion (solution will get progressively darker with time; stir until no change is apparent).
Coupling Reaction of Bovine Serum Albumin with Gd-Melanin was carried out as follows.

| Reagents: | | |
|---|---|---|
| Gd-Melanin #32.S (synthesis, see Example 26) | 10 ml | |
| 0.33M EDC | 40 µl | 192 MW |
| 0.89M DMAP | 36 µl | 122 MW |
| BSA | 25 mg | 67,000 MW |

Note: Gd-Melanin of Synthesis #32 was a >6,000 MW fraction produced from synthesis of Gd-Melanin with 1% ammonium persulfate.

This Rx solution was used for TLC analysis.
Rx 503: Synthesis of Melanin from L-Dopa and
Rx 504: Synthesis of Gd-Melanin from L-Dopa.
These reaction solutions were evaluated for T1 and T2 relaxation times.

Synthesis of Gd-Melanin (#32.S) Control solution for TLC

This solution was produced in accordance with the General Coupling Reaction procedure, except no protein was added to the solution. This was used as a TLC control solution.

More specifically, the coupling Reaction of Gd-Melanin (#32.S) to Mouse IgG was as follows:.

| Reagents: | |
|---|---|
| Gd-Melanin | 0.4 ml |
| EDC | 1.6 µl |
| DMAP | 1.4 µl |
| IgG | 1 mg |

Reaction carried out according to general procedure, except for volume adjustments.

The coupling Reaction of Gd-Melanin (#32.S) with Monoclonal Mouse Anti-BSA IgG2a (Clone BSA-33; Sigma) was carried out as follows.

| Reagents: | |
|---|---|
| Gd-Melanin | 6.1 ml |
| EDC | 24.4 µl |
| DMAP | 22.0 µl |
| BSA-33 | 0.5 ml (0.01525 g of IgG) |

Procedure

Reaction was carried out according to General Coupling Reaction procedure with the noted exception of vol:vol and wt:wt ratios. After the product was allowed to stir overnight, it was diluted to 500ml in TRIS dilution buffer solution at pH 7.4. This is equivalent to the 1:1000 solution recommended by Sigma.

An Enzyme Immunoassay (EIA) for IgG

EIA Developed for coupled IgG and may be described as follows.

This is a basic assay using concentrations recommended by the literature.

A microtiter plate was labeled with appropriate controls (-BSA, -Coupled IgG, -Conjugate). These reagents were to be omitted on the row of wells so labeled.

Procedure

Add 0.2 ml BSA Stock Soln. to wells. 0.2 ml Bovine Serum Albumin, 10µg/ml, in 0.02 M TRIS Dilution Buffer pH 7.4. BSA is the antigen for Sigma Monoclonal Mouse Anti-BSA $IgG_2A$.
Incubate overnight at 5° C.
Remove BSA from wells.
Wash 6 times with 0.2ml of TRIS Wash Buffer w/Tween. TRIS Wash Buffer is TRIS Dilution Buffer +0.5ml/L of Tween 80.

| | |
|---|---|
| 2.4 g TRIS | |
| 8.0 g NaCl | |
| 0.2 g KCl | |
| 0.5 ml Tween 80 | |
| Q5 to 1 liter and adjust pH to 7.4 with 1MHCl | |

Add 0.2ml of Coupled IgG Soln. to wells. 0.2 ml of Coupled IgG soln.=This is the Sigma Monoclonal Mouse Anti-BSA $IgG_2A$+Gd-Melanin diluted 1:1000 in 0.02M TRIS Dilution Buffer from Example 32d of outline. It functions as the test antibody in the EIA procedure.
Incubate at room temperature for 1 hour (½ recommended time interval).

Remove Coupled IgG Soln. Remove the Sigma Monoclonal Mouse Anti-BSA IgG$_2$A+Gd-Melanin from the test wells after incubation.

Wash 3 times with Wash Buffer.

Add 0.2 ml of Conjugate Soln. to wells. Bio-Rad Goat Anti-Mouse IgG Alkaline Phosphatase Conjugate diluted 1:3000 in 0.02 M TRIS Dilution Buffer. This is a Goat antibody directed against Mouse IgG, and coupled to Alkaline Phosphatase enzyme. Presence of the conjugate is revealed by the enzyme's convasion of pNPP to p-Nitrophenol.

Incubate at room temperature for 1 hour (⅓ recommended time interval).

Remove Conjugate Soln. Removal of unbound Goat anti-Mouse IgG Alkaline Phosphatase Conjugate from the test wells.

Wash 3 times with Wash Buffer.

Add Enzyme Substrate Soln. p-Nitrophenyl phosphate (pNPP): as follows:

| 1M pNPP Soln. | |
| --- | --- |
| pNPP | 15 mg |

Diluent Stock 15ml (10 mM diethanolamine, 0.5 mM MgCl$_2$, pH 9.5)

One unit of NZ activity corresponds to the hydrolysis of 1.0 μmole of pNPP per minute to p-Nitrophenol and organic phosphate, absorbance can be read at 4.05 nm (qualitatively there is a yellow color change).

Incubate 30 minutes and check for color change.

Record results.

Stop reaction with Stop Soln. 0.1 M EGTA. This was an error. Should have been 0.1 M EDTA.

EIA #1 performed.

Results indicated binding activity. Stopping Soln. did not work.

EIA #2 performed.

This was an attempt to duplicate first EIA conditions. Duplicate results were obtained.

EIA Reagent Soln. Optimization scheme developed. This is an EIA procedure using 4 BSA concentrations, 4 Conjugate concentrations, and 4 Coupled IgG concentrations; each soln. concentration vs. each soln. concentration (64 combinations) in duplicate (128 wells) to determine the optimum concentration for each soln. This test not yet performed.

EIA Buffer and Stabilizer Optimization Procedure developed. This is an EIA procedure using 2 Wash Buffers of differing Tween concentration and 3 different stabilizing (inert proteins to prevent non-specific binding); each stabilizer vs. each wash soln. and the necessary controls to determine the optimum Buffer and Stabilizer for future procedures.

All coupled melanin BSA or antibody products have shown positive EIA results indicating effective coupling and retention of antibody reactivity.

EXAMPLE 33

Mouse-imaging experiments with Gd-melanin IMAGING MEASUREMENTS: T1 weighted images (TR=450 msec, TE=30 msec) of the anesthetized rat were acquired on a GE CSI 2T/45 using a 7 cm imaging coil.

1. A forced feeding experiment was conducted where a 10 ml bolus of a sugar water solution containing gadolinium-L-DOPA-melanin (MW ca. 50,000) at 0.04 mg/ml, at two intervals thirty minutes apart, was orally administered. Images were acquired over time until the agent was cleared.

Figure 13A:
FIG. 13A,B and 13C,D illustrate MRI of coronal slices of a rat with and without the presence of orally administered (L-DOPA) melanin-gadolinium enhancing agent.
Figure 13B:
Figure 13C:
Figure 13D:

FIG. 13A represents a coronal image of a rat before oral administration of the contrast agent (see FIG. 13B for positive photocopy). FIG. 13C represents a coronal image in the same plane as FIG. 13A after the second 10 ml bolus oral administration of the melanin contrast agent (see FIG. 13D for positive photocopy). The areas of increased intensity on FIG. 13C show the location of the agent in the intestines and stomach of the rat. Note that the positive photocopy (FIG. 13D) represents the same intensified areas as darkest or of most decreased intensity because of the method used to produce an accurate, observable photocopy. As shown in these comparisons, (13A to C or 13B to D) the MRI of stomach and gastrointestinal region was greatly enhanced by melanin-Gd.

2. Feeding experiment 50 ml agent fed overnight

A feeding experiment a rat was allowed to drink ad libitum only a sugar water solution which contained gadolinium L-DOPA-melanin-Gd (MW ca. 50,000) at 0.04 mg/ml. The volume consumed during 12 hours prior to imaging was about 60 ml. Images were acquired over time until the agent was cleared.

Figure 14A:
FIGS. 14A,B illustrate and MRI examination of a rat bowel with or without ad libitum ingestion of gadolinium melanin.
Figure 14B:

FIG. 14A represents a coronal image of a rat allowed to drink the contrast solution ad libitum for 12 hours prior to imaging. See FIG. 13A for a typical rat control image. The areas of increased intensity shows the location of the agent in the intestines and stomach. FIG. 14B is the companion positive photocopy that represents the same regions as dark due to the method of reproduction. Further observations have shown that the agent clears the stomach and intestines and the images return to control images.

As shown in these comparisons, bowel MRI is greatly enhanced by Gd-melanin.

3. Rat tail vein injection—circulatory system at 30–60 min.

A 2 ml tail vein infusion of the above melanin-Gd solution was conducted in less than five minutes. Images were acquired over time until the agent was cleared.

Figure 15A:
FIGS. 15A,B represent a coronal image of a rat 60 minutes after intravenous melanin-Gd injection.
Figure 15B:
FIGS. 15C,D show a rat six days after intravenous injection of melanin-Gd indicating clearance of the agent from the system.
Figure 15C:
Figure 15D:

FIG. 15A represents a coronal image of the rat 60 minutes after infusion (see FIG. 15B for the positive photocopy). Clearly showing the location of the agent in the circulatory system (e.g. kidney, spleen). FIG. 15C shows the rat after six days indicating clearance of the agent from the system. (see FIG. 15D for the positive photocopy).

Note that the vasculature and especially the spleen is greatly enhanced by the presence of Gd-melanin in the blood stream.

What is claimed is:

1. A method of preparing an image-enhancing agent, the method comprising forming melanin from melanin precursors in the presence of paramagnetic metal at a level sufficient to form a melanin-paramagnetic metal compound where the melanin and paramagnetic metal have an association constant of at least $10^{20}$.

2. The method of claim 1 wherein the image-enhancing agent is a melanin-paramagnetic metal compound comprising at least about 1 micromole of metal per gram.

3. The method of claim 1 wherein the melanin precursors comprise a hydroxyphenyl or dihydroxyphenyl moiety.

4. The method of claim 1 wherein the melanin precursors include at least one of dihydroxyphenylalanine, catechol, dopamine, typrosine, 5,6-dihydroxyindole, 5,6-dihydroxyindole-2-carboxylic acid, 5,6-dopachrome, 5,6-indolequinone, glutathinone, cysteine, dopaquinone, 3-amino L-tyrosine and dihydroxyphenylethylamine.

5. The method of claim 1 defined further wherein the melanin-paramagnetic metal compound is bound to a water-solubilizing agent.

6. The method of claim 5 wherein the water-solubilizing agent is N-methylglucamine.

7. The method of claim 1 wherein formation of the melanin-paramagnetic metal compound is induced by a free radical generating or oxidizing agent.

8. The method of claim 7 wherein the oxidizing or free-radical generating agent is a persulfate or peroxide.

9. The method of claim 7 wherein the free radical-generating or oxidizing agent is ammonium persulfate, azobisisobutyronitrile, hydrogen peroxide, oxygen, sodium nitrite, benzoyl peroxide or t-butyl hydroperoxide.

10. The method of claim 1 wherein formation of the melanin-paramagnetic metal compound is induced by an enzyme.

11. The method of claim 10 wherein the enzyme is polyphenol oxidase.

12. The method of claim 1 wherein formation of the melanin-paramagnetic metal compound is induced by a polyphenol oxidase.

13. The method of claim 1 wherein the paramagnetic metal is gadolinium, iron, nickel, copper, erbium, europium, dysprosium, ytterbium, praseodymium, holmium, chromium, or manganese.

14. The method of claim 1 wherein the paramagnetic metal is gadolinium.

* * * * *

UNITED STATES PATENT AND TRADEMARK OFFICE
CERTIFICATE OF CORRECTION

PATENT NO. : 5,310,539

DATED : May 10, 1994

INVENTOR(S) : Williams

It is certified that error appears in the above-identified patent and that said Letters Patent is hereby corrected as shown below:

In claim 4, line 1, column 39, change "typrosine" to -- tyrosine--.

Signed and Sealed this

Ninth Day of August, 1994

Attest:

BRUCE LEHMAN

Attesting Officer

Commissioner of Patents and Trademarks